US008303518B2

(12) United States Patent
Aceti et al.

(10) Patent No.: US 8,303,518 B2
(45) Date of Patent: Nov. 6, 2012

(54) AUTONOMOUS, AMBULATORY ANALYTE MONITOR OR DRUG DELIVERY DEVICE

(75) Inventors: John Gregory Aceti, West Windsor, NJ (US); Sterling Eduard Mcbride, Princeton, NJ (US); Richard Morgan Moroney, Princeton, NJ (US); Christopher Carter Gregory, Newtown, PA (US); Peter John Zanzucchi, Princeton Junction, NJ (US)

(73) Assignee: Intuity Medical, Inc., Sunnyvale, CA (US)

( * ) Notice: Subject to any disclaimer, the term of this patent is extended or adjusted under 35 U.S.C. 154(b) by 1220 days.

(21) Appl. No.: 11/311,667

(22) Filed: Dec. 20, 2005

(65) Prior Publication Data

US 2006/0094985 A1    May 4, 2006

Related U.S. Application Data

(63) Continuation of application No. 10/131,268, filed on Apr. 23, 2002, now Pat. No. 7,004,928.

(60) Provisional application No. 60/355,195, filed on Feb. 8, 2002.

(51) Int. Cl.
*A61B 5/00* (2006.01)
(52) U.S. Cl. ........................................ 600/583; 606/181
(58) Field of Classification Search .................. 600/583; 604/180; 606/181
See application file for complete search history.

(56) References Cited

U.S. PATENT DOCUMENTS 4,254,083 A    3/1981    Columbus
(Continued)

FOREIGN PATENT DOCUMENTS

JP    9-168530    6/1997
(Continued)

OTHER PUBLICATIONS

The Diabetes Control and Complications Trial Research Group, The effect of intensive treatment of diabetes on the development and progression of long-term complications in insulin-dependent diabetes melitus: New Engl. J. Med. 1993; 329:977-986.

(Continued)

*Primary Examiner* — Max Hindenburg
*Assistant Examiner* — Renee Danega
(74) *Attorney, Agent, or Firm* — Morrison & Foerster LLP

(57) ABSTRACT

The invention relates to analyte monitoring/drug (pharmaceutical agent) delivery device. The invention is suited for monitoring various blood constituents such as glucose. The device has a housing that at least partially encloses a plurality of microneedles disposed on a carrier and an electronics portion. Each microneedle is in fluid communication with a corresponding microchannel. Each microneedle is individually addressable. That is, each microneedle can be extended and retracted individually via an actuator. The electronics portion includes a processor and associated circuitry (e.g., memory, supporting electronics and the like), a motor or the like, a sensor, a power supply (e.g., battery) and optionally an interface. In general, the processor controls the operation of the device and is data communication with the actuator, motor, sensor and interface. The invention provides for autonomous operation, that is, without intervention of the user. The invention can optionally provide for calibration without intervention of the user. The invention can also provide for semi-continuous monitoring for day and night time. The invention can provide for up to four, or more, weeks of operation. The invention can provide for a device that is relative small in size, and therefore unobtrusive. The invention can also provide for device with remote control and interactive electronics. The invention may be also used for the delivery of various pharmaceutical agents including high potency drugs to minimize patient intervention and minimize discomfort.

24 Claims, 26 Drawing Sheets

U.S. PATENT DOCUMENTS

| | | | |
|---|---|---|---|
| 4,258,001 A | 3/1981 | Pierce et al. | |
| 4,321,397 A | 3/1982 | Nix et al. | |
| 4,350,762 A | 9/1982 | De Luca et al. | |
| 4,394,512 A | 7/1983 | Batz | |
| 4,418,037 A | 11/1983 | Katsuyama et al. | |
| 4,627,445 A * | 12/1986 | Garcia et al. | 600/583 |
| 4,637,403 A | 1/1987 | Garcia et al. | |
| 4,737,458 A | 4/1988 | Batz et al. | |
| 4,774,192 A | 9/1988 | Terminiello et al. | |
| 4,790,979 A | 12/1988 | Terminiello et al. | |
| 4,815,843 A | 3/1989 | Tiefenthaler et al. | |
| 4,953,552 A | 9/1990 | DeMarzo | |
| 4,966,646 A | 10/1990 | Zdeblick | |
| 5,059,394 A | 10/1991 | Phillips et al. | |
| 5,077,199 A | 12/1991 | Basagni et al. | |
| 5,094,943 A | 3/1992 | Siedel et al. | |
| 5,116,759 A | 5/1992 | Klainer et al. | |
| 5,141,868 A | 8/1992 | Shanks et al. | |
| 5,174,291 A | 12/1992 | Schoonen et al. | |
| 5,179,005 A | 1/1993 | Phillips et al. | |
| 5,183,741 A | 2/1993 | Arai et al. | |
| 5,196,302 A | 3/1993 | Kidwell | |
| 5,208,163 A | 5/1993 | Charlton et al. | |
| 5,213,966 A | 5/1993 | Vuorinen et al. | |
| 5,234,818 A | 8/1993 | Zimmermann et al. | |
| 5,251,126 A | 10/1993 | Kahn et al. | |
| 5,278,079 A | 1/1994 | Gubinski et al. | |
| 5,288,646 A | 2/1994 | Lundsgaard et al. | |
| 5,299,571 A | 4/1994 | Mastrototaro | |
| 5,302,513 A | 4/1994 | Miike et al. | |
| 5,304,468 A | 4/1994 | Phillips et al. | |
| 5,306,623 A | 4/1994 | Kiser et al. | |
| 5,308,767 A | 5/1994 | Terashima | |
| 5,360,595 A | 11/1994 | Bell et al. | |
| 5,383,512 A | 1/1995 | Jarvis | |
| 5,390,671 A | 2/1995 | Lord et al. | |
| 5,451,350 A | 9/1995 | Macho et al. | |
| 5,458,140 A | 10/1995 | Eppstein et al. | |
| 5,460,777 A | 10/1995 | Kitajima et al. | |
| 5,482,473 A | 1/1996 | Lord et al. | |
| 5,568,806 A | 10/1996 | Cheney, II et al. | |
| 5,577,499 A | 11/1996 | Teves | |
| 5,582,184 A | 12/1996 | Erickson et al. | |
| 5,586,553 A | 12/1996 | Halili et al. | |
| 5,591,139 A | 1/1997 | Lin et al. | |
| 5,658,515 A | 8/1997 | Lee et al. | |
| 5,676,850 A | 10/1997 | Reed et al. | |
| 5,680,858 A | 10/1997 | Hansen et al. | |
| 5,681,484 A | 10/1997 | Zanzucchi et al. | |
| 5,682,233 A | 10/1997 | Brinda | |
| 5,697,901 A | 12/1997 | Eriksson | |
| 5,701,181 A | 12/1997 | Boiarski et al. | |
| 5,705,018 A | 1/1998 | Hartley | |
| 5,746,217 A | 5/1998 | Erickson et al. | |
| 5,801,057 A | 9/1998 | Smart et al. | |
| 5,807,375 A | 9/1998 | Gross et al. | |
| 5,820,570 A | 10/1998 | Erickson et al. | |
| 5,840,020 A | 11/1998 | Heinonen et al. | |
| 5,855,801 A | 1/1999 | Lin et al. | |
| 5,858,194 A | 1/1999 | Bell | |
| 5,879,326 A | 3/1999 | Godshall et al. | |
| 5,893,870 A | 4/1999 | Talen et al. | |
| 5,911,737 A | 6/1999 | Lee et al. | |
| 5,912,139 A | 6/1999 | Iwata et al. | |
| 5,925,021 A | 7/1999 | Castellano et al. | |
| 5,928,207 A | 7/1999 | Pisano et al. | |
| 5,951,521 A | 9/1999 | Mastrototaro et al. | |
| 5,971,941 A | 10/1999 | Simons et al. | |
| 5,972,294 A | 10/1999 | Smith et al. | |
| 6,001,067 A | 12/1999 | Shults et al. | |
| 6,010,463 A | 1/2000 | Lauks et al. | |
| 6,014,577 A | 1/2000 | Henning et al. | |
| 6,030,827 A | 2/2000 | Davis et al. | |
| 6,032,059 A | 2/2000 | Henning et al. | |
| 6,041,253 A | 3/2000 | Kost et al. | |
| 6,050,988 A | 4/2000 | Zuck | |
| 6,056,734 A | 5/2000 | Jacobsen et al. | |
| 6,059,815 A | 5/2000 | Lee et al. | |
| 6,077,660 A | 6/2000 | Wong et al. | |
| 6,080,116 A | 6/2000 | Erickson et al. | |
| 6,083,196 A | 7/2000 | Trautman et al. | |
| 6,090,790 A | 7/2000 | Eriksson | |
| 6,091,975 A | 7/2000 | Daddona et al. | |
| 6,100,107 A | 8/2000 | Lei et al. | |
| 6,102,933 A | 8/2000 | Lee et al. | |
| 6,103,033 A | 8/2000 | Say et al. | |
| 6,103,197 A | 8/2000 | Werner et al. | |
| 6,106,751 A | 8/2000 | Talbot et al. | |
| 6,118,126 A | 9/2000 | Zanzucchi | |
| 6,123,861 A | 9/2000 | Santini, Jr. et al. | |
| 6,126,899 A | 10/2000 | Woudenberg et al. | |
| 6,142,939 A | 11/2000 | Eppstein et al. | |
| 6,175,752 B1 | 1/2001 | Say et al. | |
| 6,183,434 B1 | 2/2001 | Eppstein et al. | |
| 6,187,210 B1 | 2/2001 | Lebouitz et al. | |
| 6,192,891 B1 | 2/2001 | Gravel et al. | |
| 6,200,296 B1 | 3/2001 | Dibiasi et al. | |
| 6,206,841 B1 | 3/2001 | Cunningham et al. | |
| 6,214,626 B1 | 4/2001 | Meller et al. | |
| 6,219,574 B1 | 4/2001 | Cormier et al. | |
| 6,228,100 B1 * | 5/2001 | Schraga | 606/183 |
| 6,230,051 B1 | 5/2001 | Cormier et al. | |
| 6,242,207 B1 | 6/2001 | Douglas et al. | |
| 6,245,215 B1 | 6/2001 | Douglas et al. | |
| 6,251,083 B1 | 6/2001 | Yum et al. | |
| 6,254,586 B1 | 7/2001 | Mann et al. | |
| 6,255,061 B1 | 7/2001 | Mori et al. | |
| 6,256,533 B1 | 7/2001 | Yuzhakov et al. | |
| 6,272,364 B1 | 8/2001 | Kurnik | |
| 6,298,254 B2 | 10/2001 | Tamada | |
| 6,299,578 B1 | 10/2001 | Kurnik et al. | |
| 6,309,351 B1 | 10/2001 | Kurnik et al. | |
| 6,312,612 B1 | 11/2001 | Sherman et al. | |
| 6,322,808 B1 | 11/2001 | Trautman et al. | |
| 6,329,161 B1 | 12/2001 | Heller et al. | |
| 6,331,266 B1 | 12/2001 | Powell et al. | |
| 6,332,871 B1 | 12/2001 | Douglas et al. | |
| 6,334,856 B1 | 1/2002 | Allen et al. | |
| 6,350,273 B1 | 2/2002 | Minagawa et al. | |
| 6,356,776 B1 | 3/2002 | Berner et al. | |
| 6,537,243 B1 | 3/2003 | Henning et al. | |
| 6,540,675 B2 | 4/2003 | Aceti et al. | |
| 6,555,061 B1 | 4/2003 | Leong et al. | |
| 6,616,616 B2 * | 9/2003 | Fritz et al. | 600/583 |
| 6,988,996 B2 * | 1/2006 | Roe et al. | 600/584 |
| 2001/0001034 A1 | 5/2001 | Douglas | |
| 2001/0053891 A1 | 12/2001 | Ackley | |
| 2002/0002326 A1 | 1/2002 | Causey et al. | |
| 2002/0002344 A1 | 1/2002 | Douglas et al. | |
| 2002/0004640 A1 | 1/2002 | Conn et al. | |
| 2002/0006355 A1 | 1/2002 | Whitson | |
| 2002/0016568 A1 | 2/2002 | Lebel et al. | |
| 2002/0020688 A1 | 2/2002 | Sherman et al. | |
| 2002/0087056 A1* | 7/2002 | Aceti et al. | 600/309 |
| 2003/0083685 A1* | 5/2003 | Freeman et al. | 606/181 |
| 2004/0092842 A1 | 5/2004 | Boecker et al. | |

FOREIGN PATENT DOCUMENTS

| | | |
|---|---|---|
| JP | 9-294737 | 11/1997 |
| JP | 10-508518 | 8/1998 |
| JP | 10-318970 | 12/1998 |
| JP | 2000-254111 | 9/2000 |
| JP | 2001-159618 | 6/2001 |
| JP | 2001-305096 | 10/2001 |
| JP | 2001-330581 | 11/2001 |
| WO | 97/29847 | 8/1997 |
| WO | 98/31275 | 7/1998 |
| WO | 00/14269 | 3/2000 |
| WO | 00/14535 | 3/2000 |
| WO | WO 00/13573 | 3/2000 |
| WO | 00/18449 | 4/2000 |
| WO | 00/74763 A1 | 12/2000 |
| WO | 00/78208 | 12/2000 |
| WO | 01/16575 | 3/2001 |
| WO | 01/52727 | 7/2001 |
| WO | 01/64105 | 9/2001 |
| WO | 01/72220 A1 | 10/2001 |

| | | |
|---|---|---|
| WO | 01/80728 | 11/2001 |
| WO | 01/91634 | 12/2001 |
| WO | 02/00101 A2 | 1/2002 |
| WO | 02/49507 | 6/2002 |

OTHER PUBLICATIONS

S. Coster, M.C. Gulliford, P.T. Seed, J.K. Powrie and R. Swaminathan, Monitoring blood glucose control in diabetes mellitus: a systematic review:, Health Technology Assessment 4(12) 2000.

W. H. Smart and K. Subramanian, "The use of silicon microfabrication technology in painless glucose monitoring", Diabetes Technology & Therapeutics 2:4, 549(2000).

M. Beregszaszi, et al., "Nocturnal hypoglycemia in children and adolescents with insulin-dependent diabetes mellitus: prevalence and risk factors", J. Pediatr. Jul. 1997; 131 (1 Pt. 1): 27-33.

H. P. Chase, et al., "Continuous subcutaneous glucose monitoring in children with type 1 diabetes", Pediatrics Feb. 2001; 107(2):222-6.

"Mosquito—A natural history of our most persistent and deadly foe", Andrew Spielman, Sc.D., Hyperion.

Su Yum, "Capillary Blood Sampling for self-monitoring of blood glucose", Diabetes Technology and Therapeutics vol. 1, Nov. 1, 1999.

P. Trinder, "Determination of glucose in blood using glucose oxidase with an alternate oxygen acceptor", Ann. Clin. Biochem. 6(1969) 24.

O. Sonntag, dry chemistry, Analysis with carrier-bound reagents, 1993 Elsevier Science Publishers, see p. 181.

ADA Consensus Development Panel, "Consensus Statement on self-monitoring of blood glucose", Diabetes Care 1987:10 95-9.

ADA Self Monitoring of Blood Glucose, A Consensus Development Conference, Diabetes Care 1994:7:81-6.

R.N. Johnson and J. R. Baker, "Accuracy of devices used for self-monitoring of blood glucose", Ann. Clin. Biochem. 1998:35:68-74.

R.N. Johnson and J. R. Baker, "Analytical error of home glucose monitors: a comparison of 18 systems", Ann. Clin. Biochem. 1999:36:72-9.

R.N. Johnson and J. R. Baker, "Error detetion and measurement in glucose monitors", Clin. Chim. Acta. 2001:307(1-2):61-7.

W. L. Clarke, D. Cox, L.A. Gonder-Frederick, W. Carter and S.L. Pohl, "Evaluating clinical accuracy of systems for self-monitoring of blood glucose", Diabetes Care 1987:10:622-8.

D.J. Cox, L.A. Gonder-Frederick, B.P. Kovatchev, D.M. Julian, W.L. Clarke, "Understanding error grid analysis", Diabetes Care 1997:20:911-12.

B. Feldman, G. McGarraugh, A. Heller, N. Bohannon, J. Skyler, E. DeLeeuw and D. Clarke, "FreeStyle.TM.: A Small-Volume Electrochemical Glucose Sensor for Home Blood Glucose Testing", Diabetes Technol. Ther. 2000:2(2):221-229.

E. Otto, C. Semotok, J. Andrysek, and O. Basir, "An intelligent diabetes software prototype: predicting blood glucose levels and recommending regimen changes", Diabetes Technol. Ther. 2000:2(4):569-576.

McGarraugh G, Price D. Schwartz S. Weinstein R., "Physiological influences on off-finger glucose testing", Diabetes Technol Ther 2001 Fall; 3(3):367-76.

Svedman C, Samra JS, Clark ML, Levy JC, Frayn KN., "Skin mini-erosion technique for monitoring metabolites in interstitial fluid; its feasibility demonstrated by OGTT results in diabetic and non-diabetic subjects", Scand. J. Clin. Lab. Invest. Apr. 1999; 59(2):115-23.

Mahler RJ, Adler ML., "Clinical review 102: Type 2 diabetes mellitus: update on diagnosis, pathophysiology, ant treatment", J. Cin. Endocrinol. Metab. Apr. 1999:84(4):1165-71.

McNichols RJ, Cote GL., "Optical glucose sensing in biological fluids: and overview", J. Biomed. Opt. Jan. 2000;5(1):5-16.

D'Arrigo, T., "GlucWatch Monitor Poised for Approval", Diabetes Forecast, Mar. 2000:43-44.

Rosen, S., "Road to New-Age Glucose Monitoring Still Rocky", Diagnostic Insight, Summer 1999:4-5, 12-13, 16.

Kumetix, Inc. "Painless Blood Glucose Monitoring Courtesy of the Mosquito", Start-Up, Dec. 1999:27-28.

Georgia Institute of Technology. Taking the "Ouch" Out of Needles: Arrays of "Microneedles" Offer New Techniques for Drug Deliver, Science Daily, Jun. 23, 1998.

Integ, Inc., Excerpts from Integ Website, 2000.

* cited by examiner

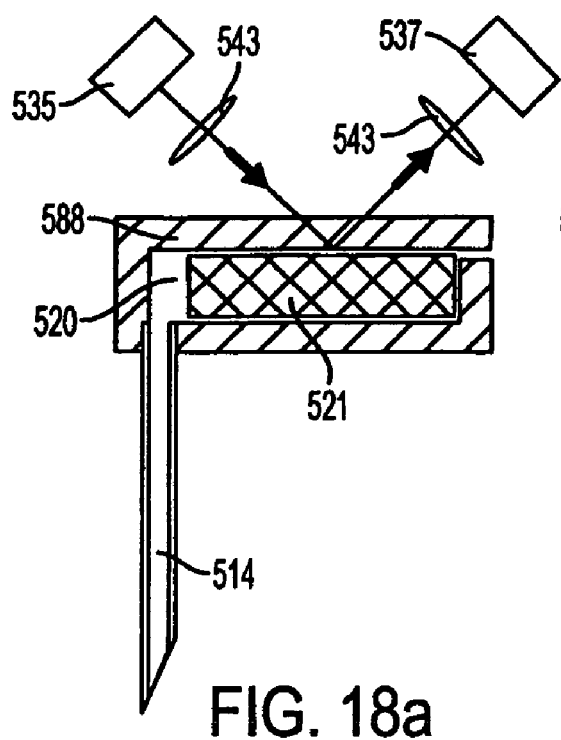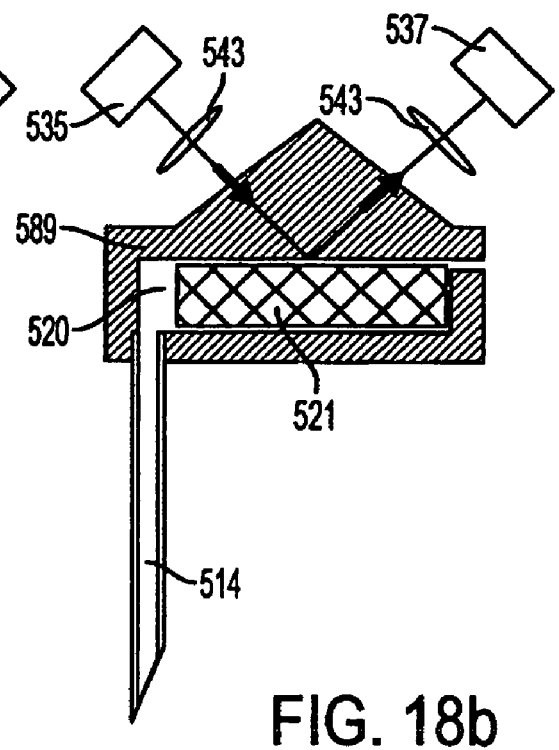
FIG. 18a  FIG. 18b
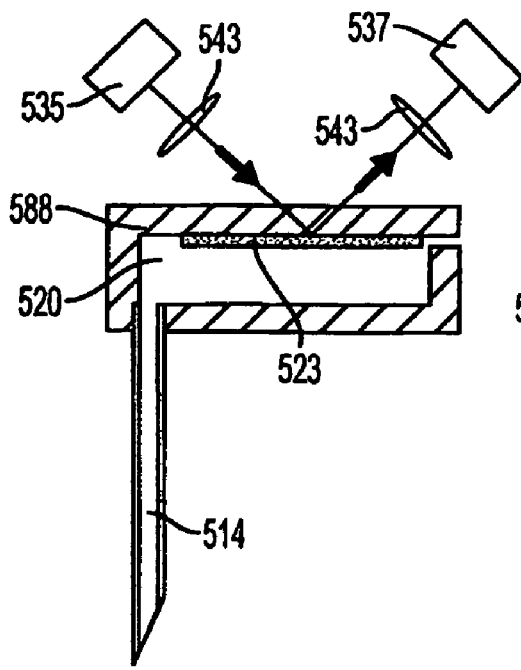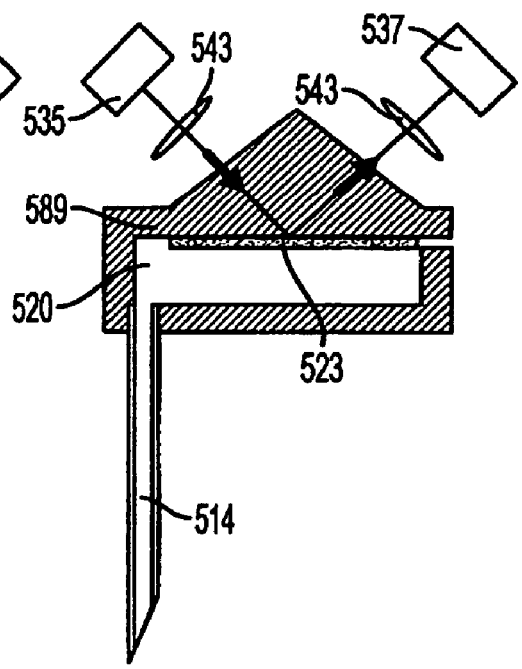
FIG. 19a  FIG. 19b

PLACEMENT OPTIONS

AUTONOMOUS, AMBULATORY ANALYTE MONITOR OR DRUG DELIVERY DEVICE

This application claims the benefit of Provisional Patent Application Ser. No. 60/355,195, filed Feb. 8, 2002.

The invention relates to the field of analyte monitoring and/or drug (pharmaceutical agent) delivery devices and in particular relates to an analyte monitoring, or drug delivery device that provides for ambulatory operation.

Home analyte monitoring is most widely used to monitor glucose by those who have diabetes mellitus. In the most serious form of diabetes mellitus, Type 1 or insulin dependent diabetes mellitus (IDDM), the pancreas fails to produce insulin. For those who have Type 1 diabetes, glucose levels must be frequently monitored in order to provide, by injection, the appropriate amount of insulin. The widespread use of home glucose monitoring reflects the fact that clinical trials have shown that frequent glucose monitoring, and good insulin maintenance, significantly reduces the loss of quality of life, and corresponding cost of care, associated with diabetes mellitus. There is a need for frequent and accurate self-testing of glucose. However, the discomfort (pain) from use of lancets and the need for manipulation of lancets, strips and hand-held monitors, often in public, significantly reduce the frequency of self-testing for glucose.

United States Patent Application No. 2002/0006355 discloses a test strip for use in the determination of the concentration of a chemical in blood. The test strip has a plurality of microneedles in fluid communication with a common test area. The microneedles are adapted to puncture skin and to draw blood. The test area contains a reagent adapted to produce a reaction indicative of the concentration of the chemical in blood.

However, in operation, the user is required to initiate a blood glucose measurement by pressing the microneedle patch onto the user's skin. Each of the microneedles lances the skin. A quantity of blood is moved by capillary action from the collection point of each microneedle to the test area. The glucose in the blood reacts with a reagent incorporated into the test chamber producing a signal indicative of the blood glucose concentration. That signal is then measured by the user with an appropriate sensor in a blood glucose analyzer (e.g., a handheld device) to determine the concentration of glucose in the user's blood. Once the blood glucose analyzer measures the signal produced by the reaction, the test strip (and microneedle patch) is discarded. Improvements in the field of analyte monitoring and/or drug delivery devices are needed.

Moreover, in the area of drug delivery, the biotechnology industry has produced important therapeutics which have unique drug delivery issues. Currently protein and peptide therapeutics are almost exclusively delivered by injection. The parenteral route, although an effective means of delivery is often viewed as complex and inconvenient to the patient. There is no better example of this that the delivery of insulin.

Accordingly, the invention relates to an analyte monitoring/drug (pharmaceutical agent) delivery device. The invention is suited for monitoring various blood constituents such as glucose. The device has a housing that at least partially encloses a plurality of microneedles disposed on a carrier and an electronics portion. Each microneedle is in fluid communication with a corresponding microchannel. Each microneedle is individually addressable. That is, each microneedle can be extended and retracted individually via an actuator. The electronics portion includes a processor and associated circuitry (e.g., memory, supporting electronics and the like), a motor or the like, a sensor, a power supply (e.g., battery) and optionally an interface.

In general, the processor controls the operation of the device and is data communication with the actuator, motor, sensor and interface. The invention provides for autonomous operation, that is, without intervention of the user. The invention can optionally provide for calibration without intervention of the user. The invention can also provide for semi-continuous monitoring for day and night time. The invention can provide for up to four, or more, weeks of operation. The invention can provide for a device that is relative small in size, and therefore unobtrusive. The invention can also provide for device with remote control and interactive electronics. The invention may be also used for the delivery of various pharmaceutical agents including high potency drugs to minimize patient intervention and minimize discomfort.

SUMMARY OF THE INVENTION

The invention relates to an analyte monitoring device operable to draw a fluid sample from a subject. The device has a first plurality of microneedles and a plurality of monitoring microchannels. Each of the first plurality of microneedles is at least intermittently in fluid communication with a corresponding monitoring microchannel. Each monitoring microchannel is also associated with a reagent. The device has at least one actuator operable to extend each microneedle to draw the fluid sample from the subject. The device also has a controller operable to initiate analyte testing of the fluid sample.

In a preferred aspect of the invention the actuator is operable to extend at least one of the first plurality of microneedles omnidirectionally. In another preferred aspect of the invention each of the first plurality of microneedles has an internal diameter in the range of about 25 to 200 micrometers. In another preferred aspect of the invention each of the first plurality of microneedles is fabricated from at least one of metal, plastic, glass and crystal. In another preferred aspect of the invention each of the first plurality of microneedles has a distal end that is operable to penetrate into a skin surface to a maximum of about 2.5 mm.

Preferably, the fluid sample is substantially blood. In another preferred aspect of the invention each of the first plurality of microneedles is at least intermittently in fluid communication with a monitoring microchannel via a conduit. In another preferred aspect of the invention each monitoring microchannel is operable to store the fluid sample and accumulation of the fluid sample in the monitoring microchannel is entirely dependent on capillary forces.

In another preferred aspect of the invention each of the monitoring microchannels has at least one internal surface that is at least partially coated with at least one insoluble material to enhance the capillary forces and minimize coagulation. In another preferred aspect of the invention the plurality of monitoring microchannels are fabricated in an array. In another preferred aspect of the invention the monitoring microchannels are fabricated in an array having approximately 50-150 microchannels formed in a maximum diameter of approximately 5 cm. In another preferred aspect of the invention each of the first plurality of microneedles is dimensioned for volumes of fluid in the range of about 50-500 nanoliters.

The device can be provided with a detector operable to determine when the fluid sample completely fills at least one monitoring microchannel such that the accumulation of the fluid sample with the associated microneedle may be terminated. In another preferred aspect of the invention at least one monitoring microchannel is in fluid communication with at least one reagent operable to assay for analytes selected from the group of (a) glucose, (b) cholesterol, (c) ethanol, (d) digoxin, (e) HDL cholesterol, (f) lithium, (g) sodium, (h) phenytoin, (i) therophylline, (j) cyclosporine, (k) cancer chemotheraphy drugs, (l) DNA, (m) RNA, (n) extended phenytonin sodium, (o) warfarin sodium, and (p) proteins derived from blood.

Optionally, at least two monitoring microchannels are associated with a single microneedle so that multiple assays can be performed using a single microneedle. In another preferred aspect of the invention a second plurality of microneedles and a plurality of calibration microchannels filled with calibration fluid, wherein at least one assay is initiated for calibration purposes.

Optionally, the device can include a third plurality of microneedles and a plurality of pharmaceutical agent delivery microchannels wherein each pharmaceutical agent delivery microchannel is at least partially filled with a pharmaceutical agent. In another preferred aspect of the invention at least one monitoring microchannel is sealed with a polymer.

In another preferred aspect of the invention the controller is operable to initiate analyte testing based on a time schedule. In another preferred aspect of the invention the controller is operable to adjust the analyte testing time schedule.

In another preferred aspect of the invention the controller is operable to couple to a portable computing device. In another preferred aspect of the invention the portable computing device is a PDA. In another preferred aspect of the invention the controller and the portable computing device is operable to select or modify times for analyte testing.

In another preferred aspect of the invention the plurality of microneedles and plurality of monitoring microchannels are disposable. In another preferred aspect of the invention the controller and the actuator are reusable. In another preferred aspect of the invention the plurality of microneedles, plurality of monitoring microchannels, actuator and controller are portable.

The device can also include a heating source operable to heat at least one injection site prior to extending a microneedle. In another preferred aspect of the invention the heating source is an optical heating source.

The device can include a housing at least partially coated with an adhesive operable to attach the housing to a surface, wherein the housing at least partially enclosing the plurality of microneedles and the monitoring microchannels. In another preferred aspect of the invention the device includes a generally disc shaped housing at least partially enclosing the plurality of microneedles and the monitoring microchannels.

The invention is also directed to a pharmaceutical agent delivery device operable to deliver a pharmaceutical agent to a subject. The device has a first plurality of microneedles and a plurality of pharmaceutical agent delivery microchannels. Each of the first plurality of microneedles is at least intermittently in fluid communication with a corresponding pharmaceutical agent delivery microchannel. Each pharmaceutical agent delivery microchannel is at least partially filled with a pharmaceutical agent. The device has at least one actuator operable to extend each microneedle to deliver the pharmaceutical agent to the subject, and. The device also has a controller operable to initiate delivery of the pharmaceutical agent.

In a preferred aspect of the invention the actuator is operable to extend at least one of the first plurality of microneedles omnidirectionally. In another preferred aspect of the invention each of the first plurality of microneedles has an internal diameter in the range of about 25 to 200 micrometers. In another preferred aspect of the invention each of the first plurality of microneedles is fabricated from at least one of metal, plastic, glass and crystal. In another preferred aspect of the invention each of the first plurality of microneedles has a distal end that is operable to penetrate into a skin surface to a maximum of about 2.5 mm.

Preferably, the fluid sample is substantially blood. In another preferred aspect of the invention each of the first plurality of microneedles is at least intermittently in fluid communication with a pharmaceutical agent delivery microchannel via a conduit. In another preferred aspect of the invention the delivery of the at least one pharmaceutical agent delivery is at least partially dependent on hydraulic forces. preferred aspect of the invention the plurality of pharmaceutical agent delivery microchannels are fabricated in an array. preferred aspect of the invention the pharmaceutical agent delivery microchannels are fabricated in an array having approximately 50-150 microchannels formed in a maximum diameter of approximately 5 cm. preferred aspect of the invention each of the first plurality of microneedles is dimensioned for volumes of fluid in the range of about 50-500 nanoliters.

The device can include a detector operable to determine when the pharmaceutical agent delivery microchannel is empty. The device can also include a third plurality of microneedles and a plurality of monitoring microchannels wherein each monitoring microchannel is associated with a reagent. Preferably, at least one pharmaceutical agent delivery microchannel is sealed with a polymer.

In another preferred aspect of the invention the controller is operable to initiate pharmaceutical agent delivery based on a time schedule. In another preferred aspect of the invention the controller is operable to adjust the pharmaceutical agent delivery time schedule.

In another preferred aspect of the invention the controller is operable to couple to a portable computing device. In another preferred aspect of the invention the portable computing device is a PDA. In another preferred aspect of the invention one of the controller and the portable computing device is operable to select or modify times for analyte testing.

In another preferred aspect of the invention the plurality of microneedles and plurality of pharmaceutical agent delivery microchannels are disposable. In another preferred aspect of the invention the controller and the actuator are reusable. In another preferred aspect of the invention the plurality of microneedles, plurality of pharmaceutical agent delivery microchannels, actuator and controller are portable.

The device can include a heating source operable to heat at least one injection site prior to extending a microneedle. In another preferred aspect of the invention the heating source is an optical heating source.

The device can also include a housing at least partially coated with an adhesive operable to attach the housing to a surface, wherein the housing at least partially enclosing the plurality of microneedles and the pharmaceutical agent delivery microchannels. The device can also include a generally disc shaped housing at least partially enclosing the plurality of microneedles and the pharmaceutical agent delivery microchannels.

The invention is also directed to the combination of a device having an analyte monitor portion operable to draw a fluid sample from a subject and a pharmaceutical agent delivery portion operable to deliver a pharmaceutical agent to the subject. The device has a first plurality of microneedles and a plurality of monitoring microchannels. Each of the first plurality of microneedles is at least intermittently in fluid communication with a corresponding monitoring microchannel. Each monitoring microchannel is associated with a reagent. The device also has a second plurality of microneedles and a plurality of pharmaceutical agent delivery microchannels. Each of the second plurality of microneedles is at least intermittently in fluid communication with a corresponding pharmaceutical agent delivery microchannel. Each pharmaceutical agent delivery microchannel is at least partially filled with a pharmaceutical agent. The device has at least one actuator operable to extend each microneedle to either draw the fluid sample from the subject or deliver the pharmaceutical agent to the subject. The device also has a controller operable to initiate analyte testing of the fluid sample and delivery of the pharmaceutical agent.

The device can also include a third plurality of microneedles and a plurality of calibration microchannels filled with calibration fluid, wherein at least one assay is initiated for calibration purposes.

The invention is also directed to a method for automated analyte monitoring. The method includes providing a first plurality of microneedles and a plurality of monitoring microchannels. Each of the first plurality of microneedles is at least intermittently in fluid communication with a monitoring microchannel. Each monitoring microchannel is associated with a reagent. The method includes sequentially extending a microneedle thereby obtaining a fluid sample from a subject and then initiating analyte testing of the fluid sample. A controller is provided to automatically repeat the sampling and testing steps.

The invention is also directed to a method for automated pharmaceutical agent delivery. The method includes providing a first plurality of microneedles and providing a plurality of pharmaceutical agent delivery microchannels. Each of the first plurality of microneedles is at least intermittently in fluid communication with a corresponding pharmaceutical agent delivery microchannel. Each pharmaceutical agent delivery microchannel is at least partially filled with a pharmaceutical agent. The method includes extending a microneedle thereby delivering the pharmaceutical agent to a subject. A controller is provided to automatically repeat the pharmaceutical agent delivery step.

BRIEF DESCRIPTION OF THE DRAWINGS

FIGS. 18a and 18b are pictorial diagrams showing another exemplary configuration for enhanced light collection using a lenses and/or a prism to improve sensitivity in accordance with the invention.

FIGS. 19a and 19b are pictorial diagrams showing yet another exemplary configuration for enhanced light collection using a lenses and/or a prism to improve sensitivity in accordance with the invention.

DETAILED DESCRIPTION OF THE INVENTION

Figure 1:
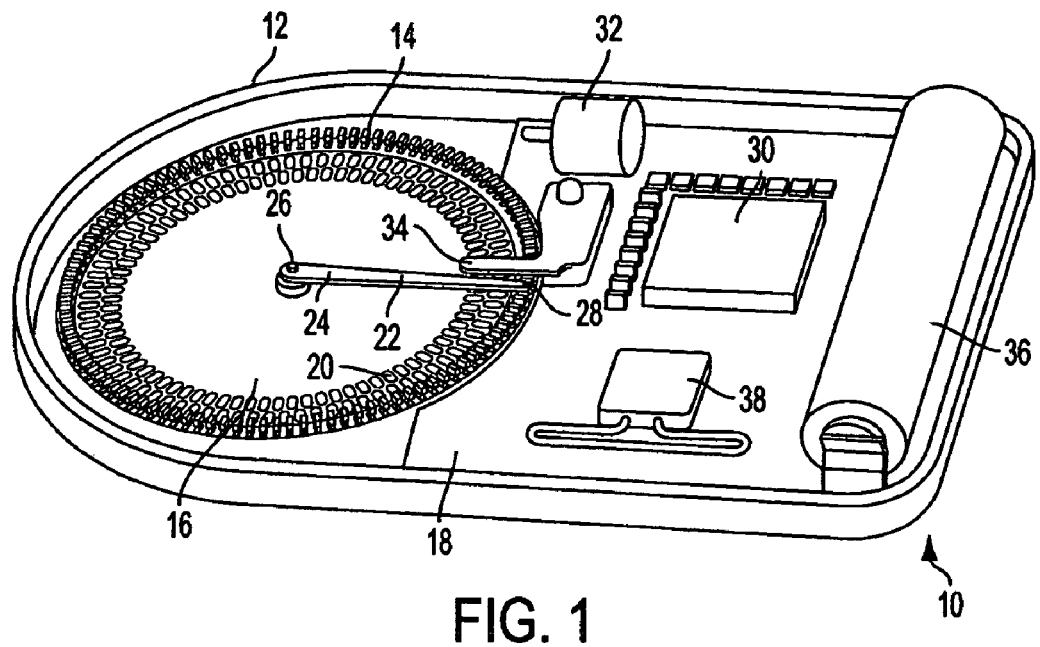
FIG. 1 is a pictorial view of a portion of an analyte monitoring/drug delivery device in accordance with the invention.

FIG. 1 shows a pictorial diagram of a portion of a analyte monitoring/drug (pharmaceutical agent) delivery device 10 in accordance with the invention. The device has a housing (lower portion only shown) 12 that at least partially encloses a plurality of microneedles 14 disposed on a carrier 16 and an electronics portion 18. The carrier 16, as shown in FIG. 1, is generally a planar substrate having a circular profile. It is understood that the carrier 16 can be formed with variety of different geometric shapes without departing from the invention.

A plurality of microchannels 20 are disposed on the carrier 16. Each microneedle 14 is in fluid communication with at least one microchannel 20. FIG. 1 shows an embodiment in which each microneedle 14 is in fluid communication with a single microchannel 20. Each microneedle 14 is individually addressable. That is, each microneedle 14 can be extended and retracted individually via an actuator. A variety of actuators are compatible with the invention.

FIG. 1 shows an embodiment in which each microneedle 14 can be extended and retracted via an actuator (a portion of which is not shown) including an arm 22 having a proximal end 24 supported by a hub 26 located generally in the center of the carrier 16. The arm 22 also has a distal end 28 that is generally disposed above a single microneedle 14.

The device also includes an electronics portion 18 having a processor 30 and associated circuitry (e.g., memory, supporting electronics and the like), a motor 32 or the like, a sensor 34, a power supply (e.g., battery) 36 and optionally an interface 38. In general, the processor 30 controls the operation of the device and is in data communication with the actuator, motor 32, sensor 34 and interface 38. Operation of the processor 30 and associated software is discussed in more detail below.

In the embodiment shown in FIG. 1, carrier 16 is movable so that each microneedle 14 is individually addressable (i.e., can be extended and retracted individually). The carrier 16 is rotatably mounted via hub 26 and is generally driven by motor 32. The connection between motor 32 and the carrier 16 can be accomplished via gears, belts and the like as discussed in more detail below. The interconnection of movable carriers and drive mechanisms suitable for use in conjunction with the invention based on the disclosure herein is well within the scope of one skilled in the art.

Figure 2:
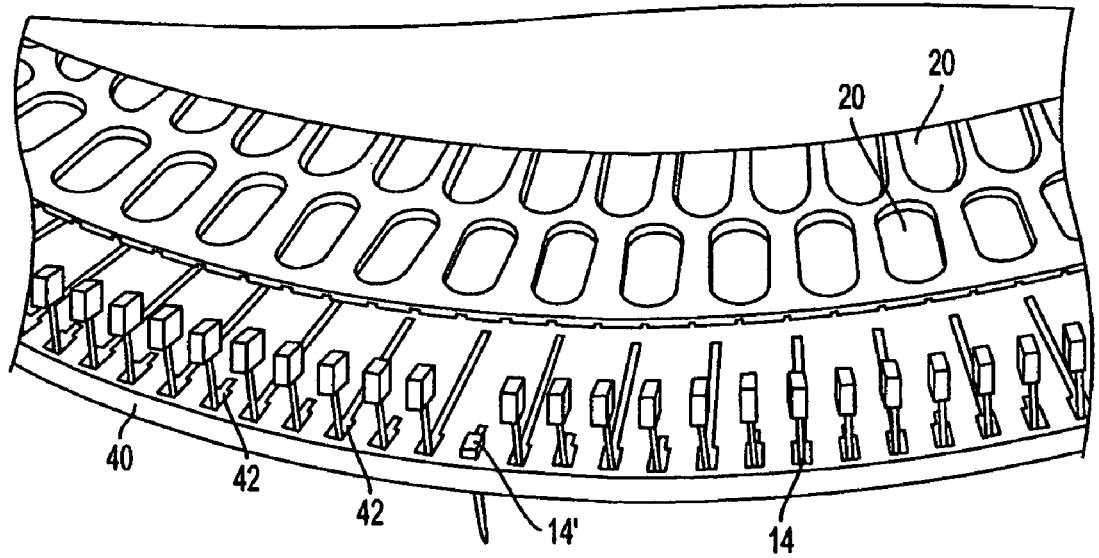
FIG. 2 is a pictorial view showing additional structural details of the carrier microneedles, microchannels and conduit in accordance with FIG. 1.

FIG. 2 shows some of the structural details of the carrier 16 shown in FIG. 1. The carrier 16 has a plurality of microneedles disposed generally adjacent to an edge 40. Microneedle 14' is shown in the extended position (the actuator is not shown). Each microneedle 14 generally has an internal bore in fluid communication with a microchannel 20 via a conduit 42. FIGS. 1 and 2 show microchannels that are generally disposed along a radial line extending between the hub 26 (disposed on a central axis) and the associated microneedle. The microchannels are generally shown in a nested configuration (i.e., two rows). This configuration is advantageous since it allows for microchannels that are generally wider than the microneedles and provides for increased microneedle density (i.e., more closely spaced microneedles) at the peripheral edge 40 of the carrier 16. It is understood that microchannels 20 can be positioned in a variety of geometric configurations without departing from the scope of the invention. It is also understood that conduits 42 can be routed in a variety of geometric configurations as necessary to link with the microchannels 20.

Figure 3:
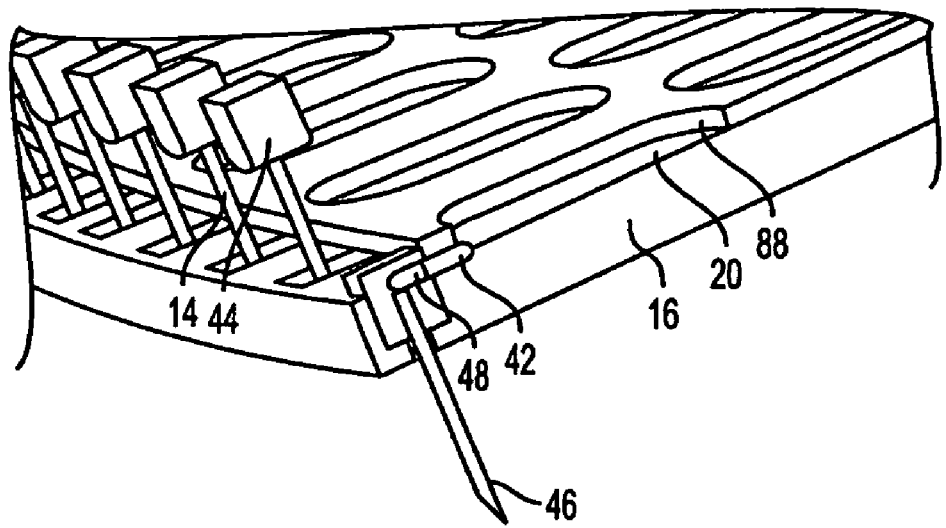
FIG. 3 is a pictorial view showing additional structural details of the carrier microneedles, microchannels and conduit in accordance with FIGS. 1 and 2.

FIG. 3 shows additional structural details of the carrier 16, microneedles 14, microchannels 20 and conduits 42 generally in accordance with FIGS. 1 and 2. Microchannel 20 is preferably provided with a cover 88. Preferably the cover is at least partially translucent or transparent to facilitate optical detection of assays. The cover generally protects the contents of the microchannel from contamination. The cover can be generally rigid or flexible as discussed in more detail below.

Each microneedle 14 is formed with a proximal end 44 that interfaces with the microchannel 20, and a distal end 46 operable to penetrate the tissue or skin (for collecting a sample of blood or delivering a drug or pharmaceutical agent). The proximal end 44 is formed with an opening 48 that generally couples to the conduit 42.

In operation, a single microneedle 14 is moved into the extended position and penetrates the skin. Opening 48 is aligned with conduit 42 coupling the microneedle 14 with the microchannel 20 in fluid communication. The device is generally operable to function as a monitor and collect a sample of blood to be analyzed. The device is also operable to deliver a drug or pharmaceutical agent. Each microneedle 14 can be designated for monitoring or drug delivery. For monitoring, microneedle 14 is preferably associated with a "monitoring microchannel" configured for a specific assay technique (e.g., having a reaction layer) as discussed in more detail below. For drug delivery, microneedle 14 is preferably associated with a "pharmaceutical agent delivery microchannel" that is at least partially filled with the drug or pharmaceutical agent to be delivered as discussed in more detail below.

Figure 4:
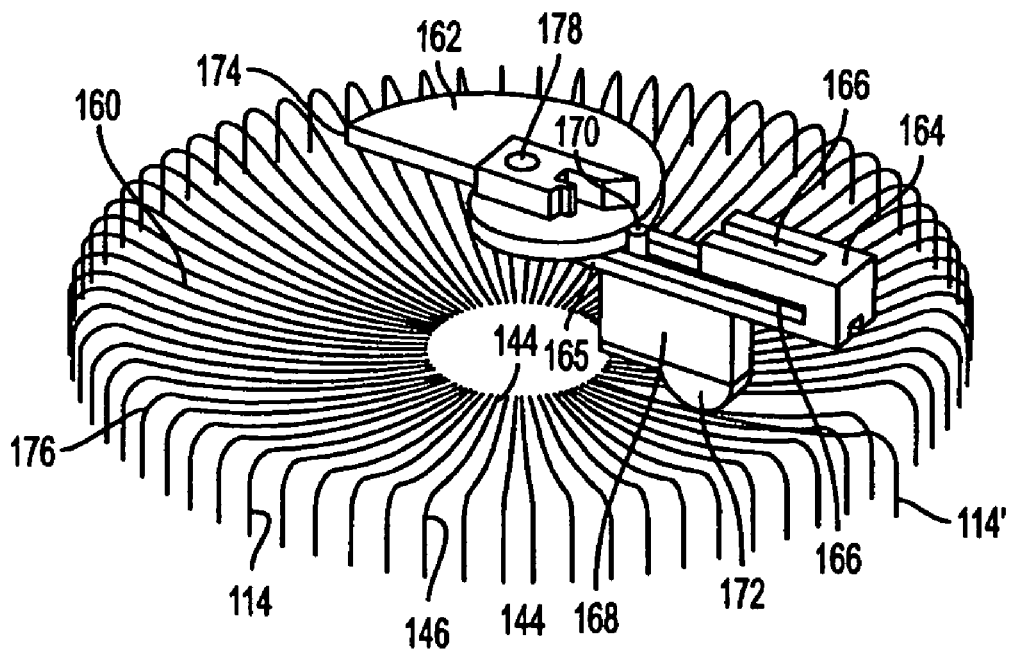
FIG. 4 shows an alternate embodiment of an analyte monitoring/drug delivery device in accordance with the invention.

FIG. 4 shows an alternate embodiment of a device. In this embodiment, the plurality of microneedles 114 and the carrier (not shown) are generally stationary with respect to the housing (not shown). The microchannels are not shown although the location and interconnection of microchannels for use in conjunction with this embodiment of the invention based on the disclosure herein is well within the scope of one skilled in the art.

Each microneedle 114 has a proximal end 144 extending towards a central axis 178 and distal end 146 directed downward (i.e., directed at the skin or tissue). The proximal end 144 of each microneedle 114 is preferably anchored or coupled to the carrier. Each microneedle 114 generally includes a curve or bend 176 thereby defining a ramp portion 160 formed between the proximal and distal ends. In this embodiment, the anchored proximal end 144 and ramp portion provide an incline used to extend the microneedle 114 as well as a spring biasing of the microneedle in the retracted position. Other arrangements for spring biasing the microneedle are readily apparent to those skilled in the art.

The actuator includes a cam 162, a track 164 formed with slots 166 and a slider 168 having an index pin 170. The actuator also includes a motor (not shown) or the like for driving or rotating the cam about the central axis 178. The connection between such a motor and the cam 162 can be accomplished via gears, belts and the like as discussed in more detail below. The interconnection of cam and drive mechanisms suitable for use in conjunction with the invention based on the disclosure herein is well within the scope of one skilled in the art.

The slider 168 is movable between a retracted position (closer to the central axis) and an extended position (further from the central axis). In the retracted position, the slider is disposed generally above the ramp portion 160 of at least one microneedle 114 and preferably does not contact the microneedle. The slider is also preferably biased or spring loaded in the retracted position. Biasing mechanism or springs are not shown. However, the biasing mechanisms or spring loading of a slider for use in conjunction with the invention based on the disclosure herein is well within the scope of one skilled in the art. The slider shown in FIG. 4 is generally shown between the retracted and extended position.

As cam 162 rotates, it pushes the slider 168 outward along the track 164. The slider has a lower portion 172 operable to contact a single microneedle 114 as the slider moves from the retracted position to the extended position. The index pin 170 is slidably engaged in slots 166, thereby restricting the slider to motion along a linear path (along the ramp portion 160 of a single microneedle 114). As the slider moves along the ramp portion 160, the distal end 146 of the microneedle 114 is forced downward (e.g., into the tissue for collecting a sample or delivering a pharmaceutical agent). Once the cam reaches its maximum lobe height 174, the slider 168 returns to the retracted position allowing microneedle 114 to respond to spring biasing forces and withdraw from the tissue.

The track 164 generally has a proximal end 165 that is pivotally engaged along the central axis. Once the slider 168 returns to the retracted position allowing microneedle 114 to spring out of the tissue, track 164 is then advanced (i.e., rotated clockwise or counter-clockwise) to index or address to the next microneedle 114. The cycle can then be repeated.

It is understood that microneedles 114 do not have to be continuous in structure. For example, a fluidic capture and processing site can be located at the bend 176 of each microneedle 144. This site can interface with a fluidic layer positioned below the microneedles. When the microneedle is fully depressed, it preferably aligns with the fluidic processing layer forming a continuous fluid path. This path preferably remains sealed until the microneedle 114 is pressed down.

Figure 5:
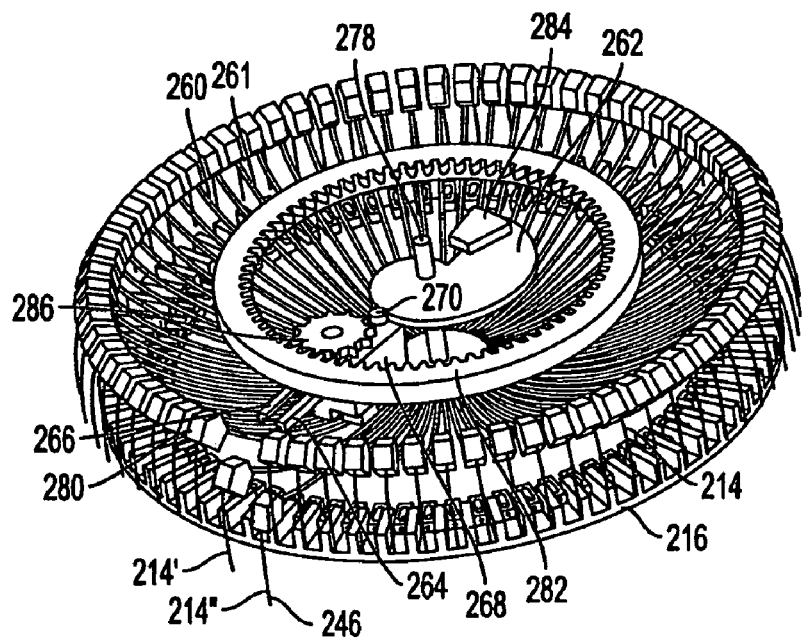
FIG. 5 shows another alternate embodiment of an analyte monitoring/drug delivery device similar to the device shown in FIG. 4 also incorporating a fluidic capture and processing site in accordance with the invention.

FIG. 5 shows another alternative embodiment of a device incorporating a fluidic capture and processing site as discussed above. In this embodiment, the plurality of microneedles 214 and the carrier 216 are generally stationary with respect to the housing (not shown). Each microneedle 214 has a distal end 246 directed downward (i.e., directed at the skin or tissue) and a proximal end 244 engaged in fluidic capture site 280. A spring member 261 is coupled between the fluidic capture site 280 and the carrier 216 thereby defining a spring biased ramp portion 260.

The actuator includes a cam 262 having a tooth 284, a track 264 formed with at least one slot 266 and a slider 268 having an index pin 270. The actuator also includes a ring gear 282 that is coupled to housing (not shown) and is generally stationary with respect to the track 264. As discussed above, the track 264 is pivotable around the central axis 278. The actuator also includes an idler gear 286 that driven by the tooth 284 as discussed in more detail below. Idler gear 286 has a pivot point that is anchored to the track 264, and generally moves the track in an incremental fashion, to index or address successive microneedles 214.

The slider 268 is movable between a retracted position (closer to the central axis) and an extended position (further from the central axis). In the retracted position, the slider is disposed generally above the ramp portion 260 of at least one microneedle 214 and preferably does not contact the microneedle. The slider is also preferably biased or spring loaded in the retracted position. Biasing mechanism or springs are not shown. However, the biasing mechanisms or spring loading of a slider for use in conjunction with the invention based on the disclosure herein is well within the scope of one skilled in the art. The slider shown in FIG. 5 is generally shown in the retracted position. Microneedles 214' and 214" are shown in an intermediate position and the extended positions respectively for illustrative purposes only.

As cam 262 rotates (clockwise), it pushes the slider 268 outward along the track 264. The slider has a lower portion operable to contact a single microneedle 214 as the slider moves from the retracted position to the extended position. The index pin 270 is slidably engaged in slot 266, thereby restricting the slider to motion along a linear path (along the ramp portion 260 of a single microneedle 214). As the slider moves along the ramp portion 260, the distal end 246 of the microneedle 214 is forced downward (e.g., into the tissue for collecting a sample or delivering a pharmaceutical agent).

Once the cam reaches its maximum lobe height, the slider 268 returns to the retracted position allowing microneedle 214 to spring out of the tissue. Tooth 284 engages the idler gear 286 and advances the gear by one tooth. Track 264 is then advanced (i.e., rotated counter-clockwise) to index or address to the next microneedle 214. The number of teeth on idler gear 286 and ring gear 282 are selected so that each single tooth movement of the idler gear 286 results in the proper angular displacement of the track 264 to precisely index or address the next microneedle 214. The cycle can then be repeated.

Figure 6:
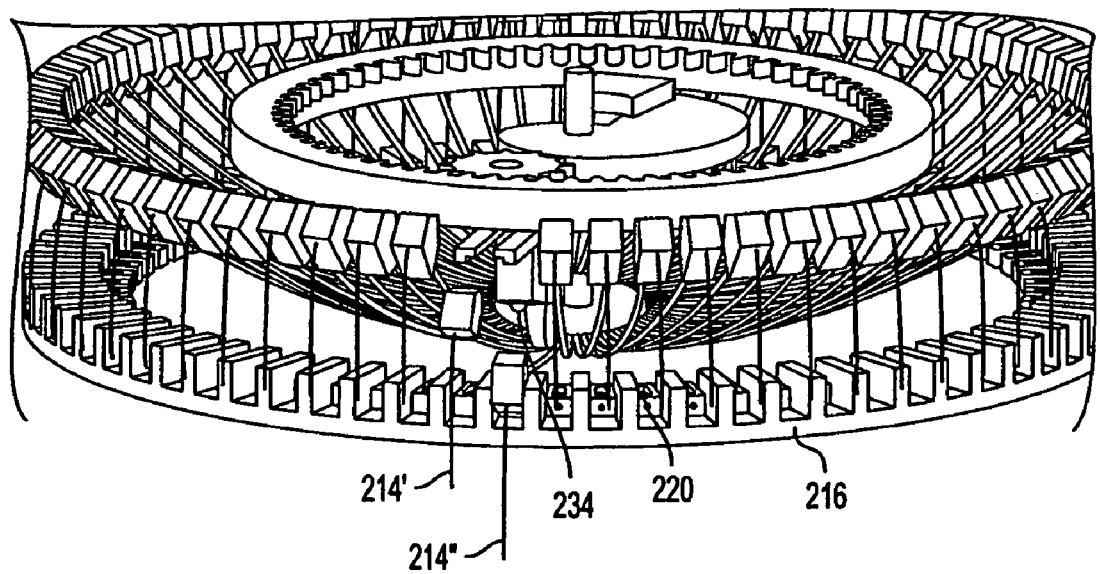
FIG. 6 is a pictorial view showing additional details of the embodiment shown in FIG. 5 in accordance with the invention.
Figure 7:
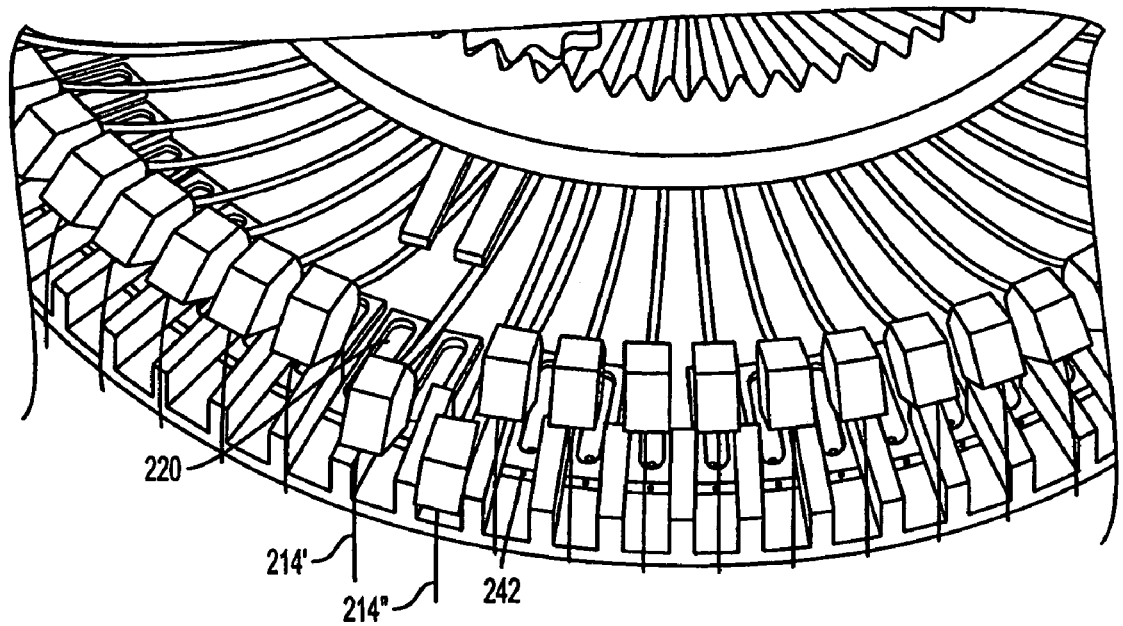
FIG. 7 is a pictorial view showing additional details of the embodiment shown in FIGS. 5 and 6 in accordance with the invention.
Figure 8:
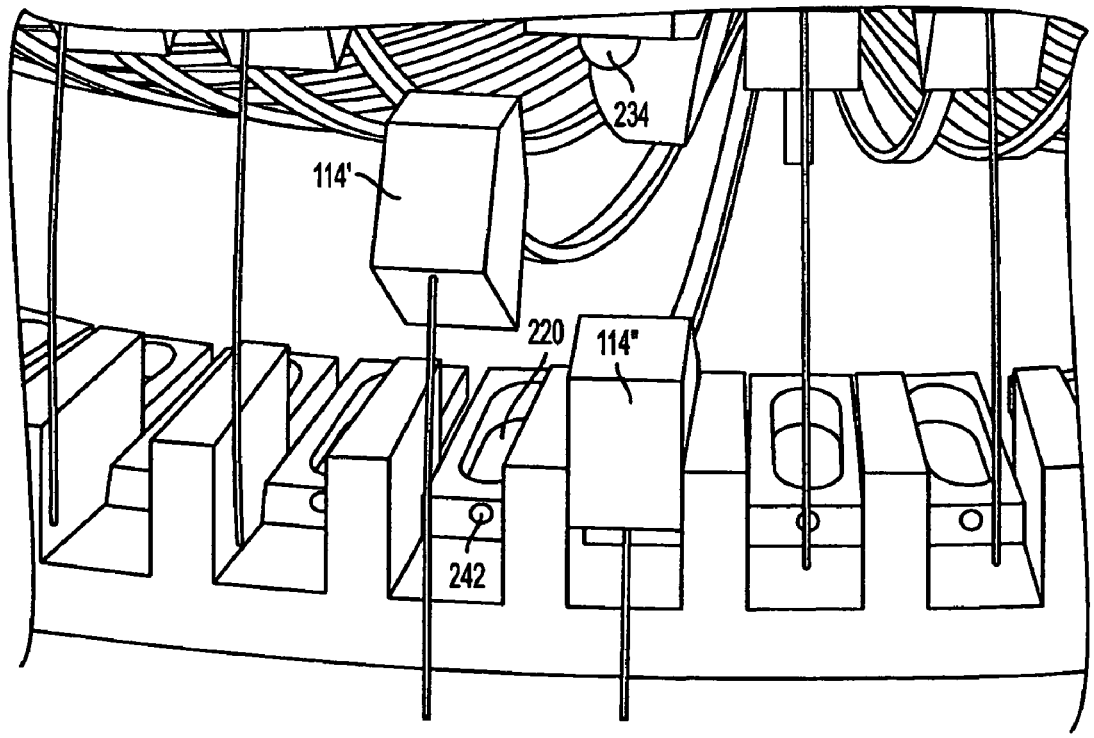
FIG. 8 is a pictorial view showing additional details of the embodiment shown in FIGS. 5-7 in accordance with the invention.

FIGS. 6-8 are pictorial views showing additional details of the embodiment shown in FIG. 5. Continuing with the discussion above, once microneedle 214 is in the extended position, the proximal end of the microneedle 244 and fluidic capture site 280 interfaces with a microchannel 220. The fluidic capture site is formed with an opening that generally couples to a conduit 234 and ultimately microchannel 220 as discussed with respect to FIG. 3.

In a monitoring configuration, depression of microneedle 214 results in the collection of blood in microchannel 220. Microchannel 220 is preferably configured for a specific assay technique (e.g., having a reaction layer) as discussed in more detail below. The reaction is preferably monitored by sensor 234 mounted to the 268 slider generally disposed above microchannel 220.

Microchannel 220 is preferably provided with at least some form of cover. Preferably the cover is at least partially translucent or transparent to facilitate optical detection of assays. See e.g., cover 88 in FIG. 3. The cover generally protects the contents of the microchannel from contamination. The cover can be generally rigid or flexible. For delivery of a drug or pharmaceutical agent, the drug is preferably fluid is stored in a compressible microchannel (e.g., a microchannel having a flexible cover). As the slider 268 moves towards the extended position it preferably presses the microneedle 214 into the skin or tissue. As the microneedle is inserted the slider can at least partially compressing microchannel 220 and forcing the fluid out through the conduit 242 and ultimately the microneedle 214 and into the skin or tissue. It is understood that both monitoring and drug delivery be carried out within the same device by allocating a portion of microneedles 214 for each task.

It is also understood that other mechanisms can be used to facilitate delivery of pharmaceutical agents. For example, a small fluidic pump can provide positive pressure to the microchannel. The pharmaceutical agent contained in the microchannel is then expelled through the through the microneedle. Optionally, a capacitance detector can be used to sense that the microchannel is empty and can signal that the fluidic pump should be turned off, thereby controlling the possibility of air entering the delivery system.

Figure 9:
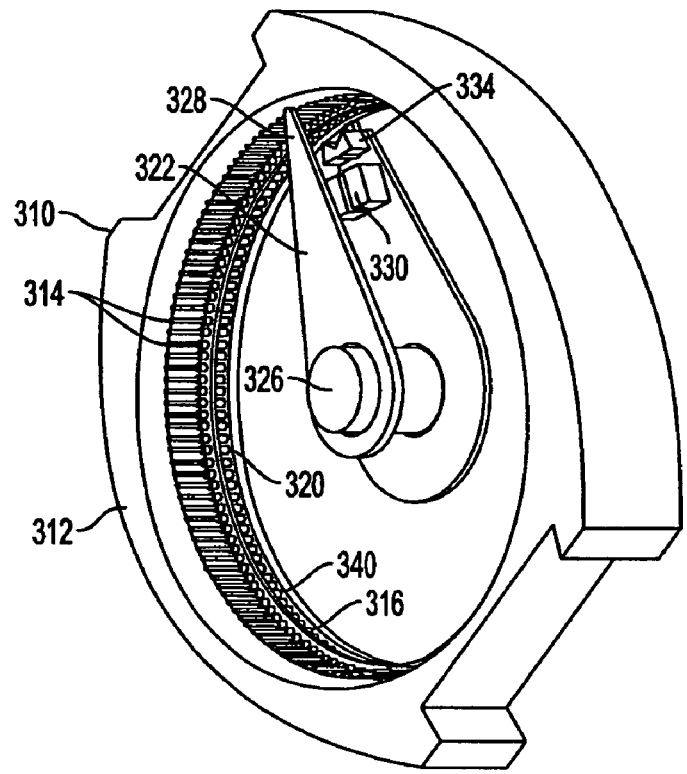
FIG. 9 shows another alternate embodiment of an analyte monitoring/drug delivery device in accordance with the invention.

FIG. 9 shows another alternative embodiment of a device 310 in accordance with the invention. The device has a housing (only partially shown) 312 that at least partially encloses a plurality of microneedles 314 disposed on a carrier 316. The carrier 316 is generally a planar substrate having a ring-like profile. It is understood that the carrier 16 can be formed with variety of different geometric shapes without departing from the invention.

A plurality of microchannels 320 are disposed on the carrier 316. In this embodiment, the 388 cover is arranged on an inside edge 340 of the substrate 316. Each microneedle 314 is preferably in fluid communication with a single microchannel 320. Each microneedle 314 is individually addressable.

FIG. 9 shows an embodiment that is somewhat similar to FIG. 1 in that each microneedle can be extended and retracted via an actuator (a portion of which is not shown) including an arm 322 having a proximal end supported by a hub 326 located generally in the center of the device. The arm 322 also has a distal end 328 that is generally disposed above a single microneedle 314.

The device also includes an electronics portion having a processor 330 and associated circuitry (e.g., memory, supporting electronics and the like), a motor or the like (not shown), a sensor 334, a power supply or battery (not shown) and optionally an interface (not shown).

In the embodiment shown in FIG. 9, the plurality of microneedles 414 and the carrier 316 are generally stationary with respect to the housing 312. The connection between the drive motors and the arm 322 is not shown. This can be accomplished via gears, belts and the like as discussed above. The interconnection of the microchannels 320, microneedles 414, conduits, drive mechanisms and the like in conjunction with the invention based on the disclosure herein is well within the scope of one skilled in the art.

Exemplary System Segmentation

Figure 27:
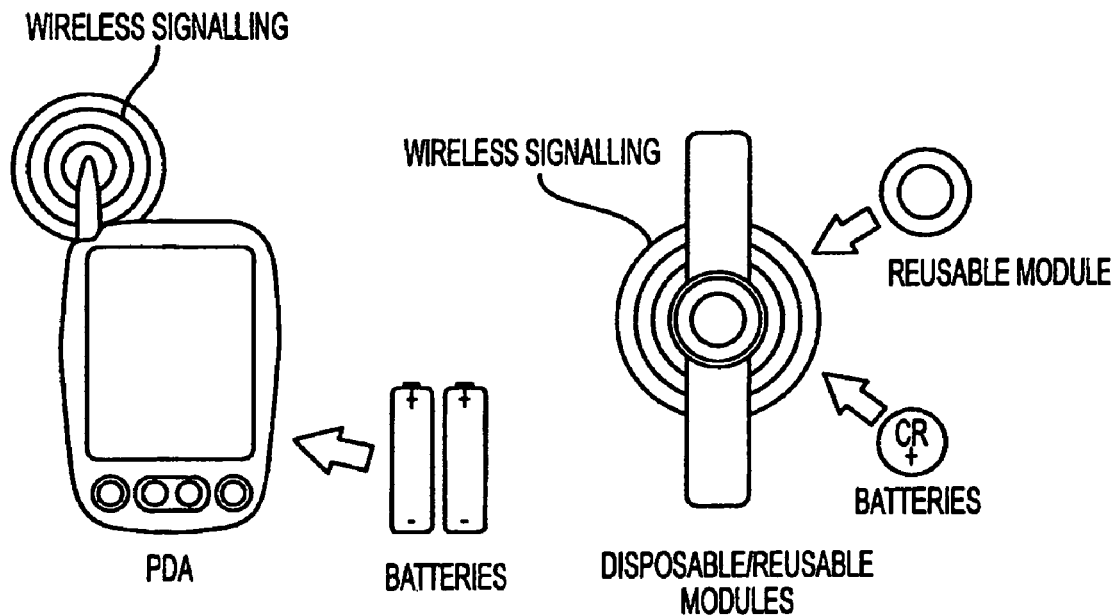
FIG. 27 is a pictorial diagram showing an exemplary PDA, Disposable and Reusable module in accordance with the invention.

Three exemplary system modules have been identified to optimally meet the requirements of a user friendly, diagnostically relevant, and low cost analyte monitoring/drug (pharmaceutical agent) delivery system. The analyte monitoring/drug (pharmaceutical agent) delivery system is preferably partitioned into a Disposable Module, a Reusable Module and a PDA Module. See e.g., FIG. 27. This configuration optimally distributes functionality amongst these three configurations to achieve certain advantages. However the invention is not limited to this configuration. For example, a one-unit disposable device including all electronics, microneedles, chemistry, mechanics and user interface may be alternatively employed. Or, more relevantly, the design of the invention allows for any distribution of components between one or more system modules. For example, components may be partitioned among one or more system modules based on the overall system cost, user safety and/or performance concerns.

The Disposable Module—This module contains those components that once used must be discarded to maintain biological safety and diagnostic accuracy. This module preferably includes any structural or mechanical elements to maintain integrity, sterility and an electromechanical interface to any reusable components. Therefore this system module preferably includes: microneedles, a microfluidic assembly, membrane, reagent chemistry and associate housing materials. This module can also include retaining mechanisms for establishing and maintaining intimate contact with the body thereby providing mechanical retention of the analyte monitoring/drug (pharmaceutical agent) delivery system.

The Reusable Module—This module preferably contains those components that control, automate motion, measure the glucose reaction, alarm the user, transmit data to the PDA module. This module can also include retaining mechanisms for establishing and maintaining intimate contact with the body thereby providing mechanical retention for the analyte monitoring/drug (pharmaceutical agent) delivery system. Preferably, this module includes: a microprocessor with associated circuitry (e.g., memory, supporting electronics and the like), a sensor (e.g., an electro-optical sensor) for evaluating the products of any reactions (e.g., glucose reactions), drive mechanisms such as motors or the like, a sensor, a power supply (e.g., battery) 36 and an interface operable to communicate with a portable computing device or PDA. The interface can be RF, magnetic or inductive, optical or the like. Using magnetic or inductive coupling rather than RF coupling is advantageous since it can potentially avoid FCC restrictions or limitations. The reusable module can also an audible or vibration alarm to notify the user that user action intervention is required.

The PDA Module—This module preferably includes a separate user interface via a portable computing device such as a personal digital assistant (PDA), handheld computer or the like for controlling and/or interacting with the device. A typical portable computing device includes a processor, memory, associated circuitry, a display (e.g., monochrome or color LCD) and an input device such as a key pad, touch screen (e.g., integrated with the display) or the like and an operating system. Previously available glucose monitors were specifically designed for handling the paper test strips, for viewing numerical values of the glucose measurements and for setting other parameters of the meter such as its calibration. These custom designed units had limited functionality and relatively crude user interfaces.

Today, portable computing devices with improved operating system software and user interfaces are readily available. These devices provide the potential for richer and extended functionality. For example a typical PDA includes a relatively large viewing screen (important to the many diabetic elderly) and can also include wireless communications mechanisms, a sophisticated operating system and a variety of business and personal software (calendars, scheduling, etc.). Accordingly, a PDA provides a robust platform for developing diabetic related software. Recently the FDA approved the first PDA for monitoring EKG activity. The invention preferably includes the use of a PDA to provide the proprietary software (programs) for autonomous operation with an improved user interface.

To this end, the PDA module preferably provides the user with software that facilitates informed decisions to help the diabetic user more optimally adjust either drug or dietary consumption to more optimally control glucose. The PDA configuration provides a user interface and preferably allows users the ability to program and or control testing. The user can view individual glucose measurements and graphically display glucose value trends by the day, week or custom time period. The PDA can be used to display any and all of the measurements recorded by the system. Using the proper software, the user can be provided with recommendations for drug regiment modification (insulin or other). The user can also be provided with recommendations for dietary changes. See FIG. 25. The PDA can also store grocery lists for daily menus. The grocery list can be viewed by the user as needed to ensure proper dietary intake.

Figure 24:
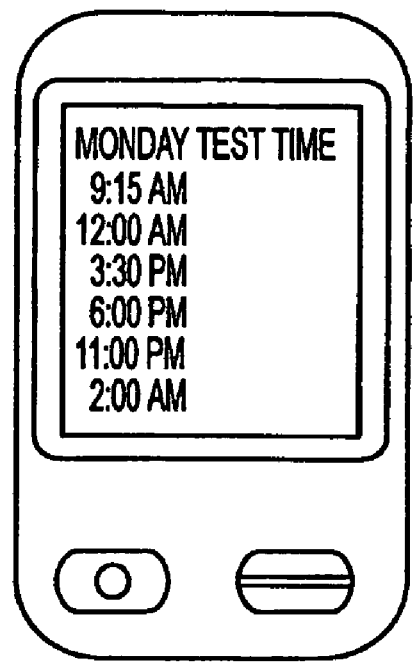
FIG. 24 is a pictorial diagram showing an exemplary PDA display showing test times in accordance with the invention.

The user can preferably program the times when their analyte tests are to be taken. Preferably, the user can also set the upper and lower limits for alerts. As shown, a graphic showing a clock can be easily used to select or modify times for testing. See FIG. 24.

Whenever the user makes changes and with verification from the user, the information is wirelessly downloaded to the system. During the day the user will not need to use the PDA unless alerted by the system to check for an analyte reading. The user can initiate a test from the PDA if wanting to make an immediate measurement. Once the user selects this command, verifies it, and transmits it to the Reusable, a confirmation is made back to the PDA.

An increased number of tests per day can be accommodated for a shorter use life. For example, a newly diagnosed diabetic can have a 24 test per day regiment for the first 6 days to ascertain maximum peaks and lows with various daily regiments of exercise, stress and food types. Then with the user profiled, the caregiver may reduce the number of tests to an appropriate level. Additional aspects of the PDA module and associated software is discussed below.

Exemplary Microneedle Structures

The invention encompasses mechanisms operable to extend a microneedle that is smaller than most used today, for injection or blood extraction (referred to herein as a microneedle). The use of microneedles allows for the extraction of blood with minimal discomfort or pain. It has been noted that blood extraction by the mosquito is efficient. This insect has managed to do what man cannot, that is, to extract blood essentially without pain while drawing blood through a micrometer hollow member.

The mosquito accomplishes blood extraction by use of a proboscis which consists of two tubes surrounded by two pairs of cutting stylets that are together in a tight bundle. This bundled entity is called the fascicle and the bundle is about 40 to 60 micrometers in diameter. The fascicle breaks the skin surface of the victim with its stylets. Once below the surface, the fascicle bends at a sharp angle to begin exploring for blood. With each insertion, the mosquito attempts to hit a venule or arteriole. On each try, the mosquito will withdraw the fascicle slightly while leaving it in the original hole, and angle it in a different direction. Once blood is found, the mosquito may draw blood for about ninety seconds and will draw a few micrograms, e.g., 5 microliters, of blood. The invention encompasses technology that mimics the function of the mosquito and within the disclosed analyte monitor/drug delivery system.

The diameter of a microneedle is, for example, optimally about 40 to 120 micrometers, approximately the size of the mosquito's proboscis. Preferably, the microneedle is driven into the skin or tissue to a depth to yield a sample that is mostly blood with minimal interstitial fluid. The microneedle preferably has an internal diameter of about 25 to 100 micrometers, sufficient for blood to flow freely and, preferably, to flow by capillary action. Needles of this type have been demonstrated by Kumetrix, Inc. (e.g., a MEMS based silicon microneedle having an internal microfluidic channel approximately 25 micrometers in width, providing very strong capillary forces but allowing the erythrocytes to flow without difficulty).

The invention is alternatively operable with standard hypodermic tubing rather than silicon MEMS microneedles (e.g., to achieve sufficient strength at low cost). Hypodermic tubing is currently available in sizes down to 75 micrometers in diameter. Alternatively the microneedles can be made from glass and drawn to thin diameters similar to the way hollow capillary tubing is drawn. It is understood that microneedles suitable for use in conjunction with the invention can be fabricated by a variety of methods. It is also understood that microneedles suitable for use in conjunction with the invention can be fabricated from a variety of materials including, but not limited to, metal, plastic, glass and crystal (e.g., quartz).

Figure 11:
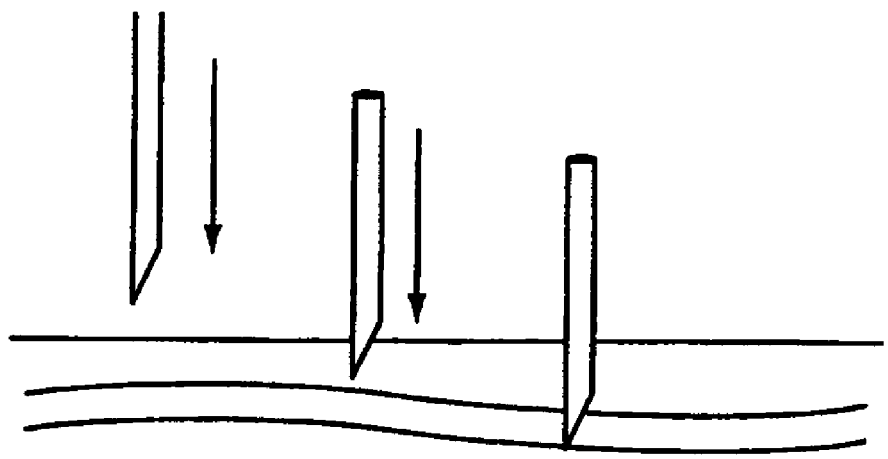
FIG. 11 is a pictorial diagram showing a straight microneedle with orthogonal entry in accordance with the invention.

The microneedle can be either straight or curved and enter the skin rectilinearly, curvilinear or obliquely. Orthogonal entry with rectilinear motion is potentially the simplest to achieve, advantageously requiring a minimal length of tubing below the epidermis. See FIG. 11. A potential disadvantage is that the minimum length may fail to erupt or puncture enough blood vessels to cause blood to flow in sufficient volume. Entering the skin obliquely increases the number of potential blood vessels skewered but may aggravate more nerve endings. Making the microneedle curved also tends to access more tissue and can enhance collection by crossing more blood vessels without penetrating deeply. The orthogonal method will be optimal where blood is acquired readily and where nerve ending are rich. The oblique or curved microneedle approach is optimal where nerve fibers are less dense.

Figure 12:
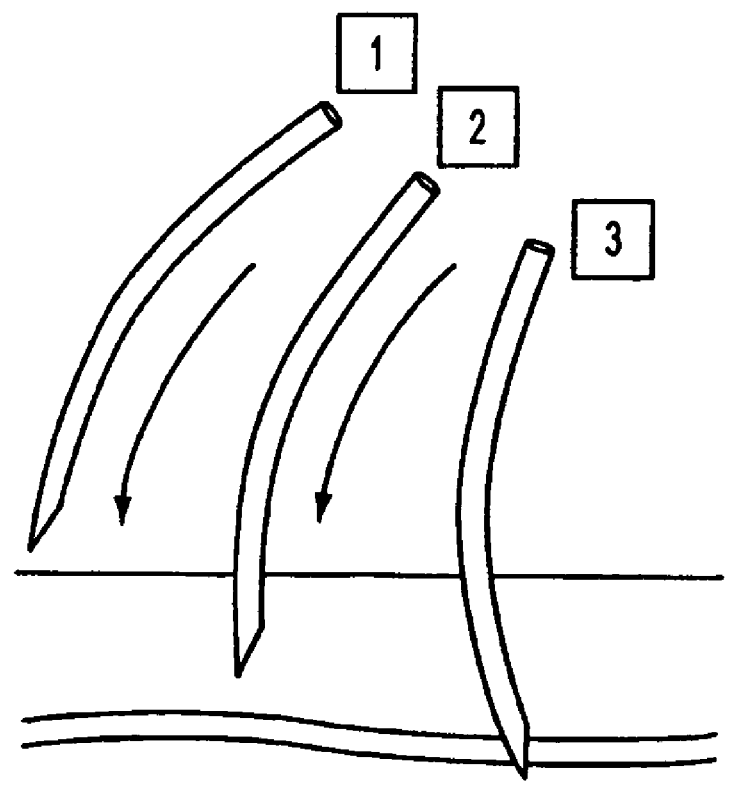
FIG. 12 is a pictorial diagram showing a curved microneedle with orthogonal entry shown in three sequential positions in accordance with the invention.
Figure 13:
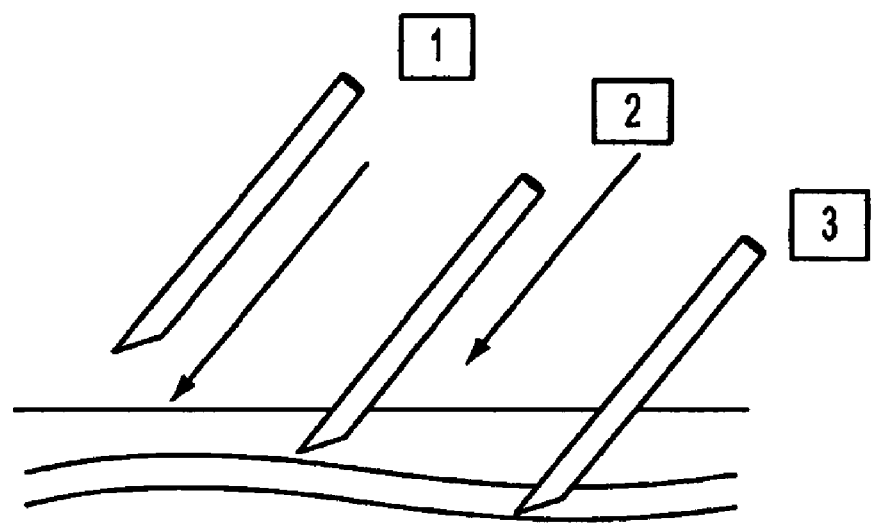
FIG. 13 is a pictorial diagram showing a straight microneedle with angled entry shown in three sequential positions in accordance with the invention.
Figure 14:
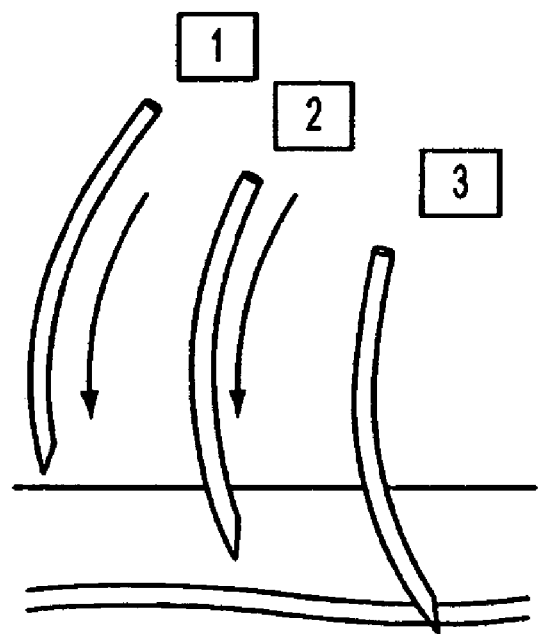
FIG. 14 is a pictorial diagram showing a curved microneedle with angled entry shown in three sequential positions in accordance with the invention.
Figure 15:
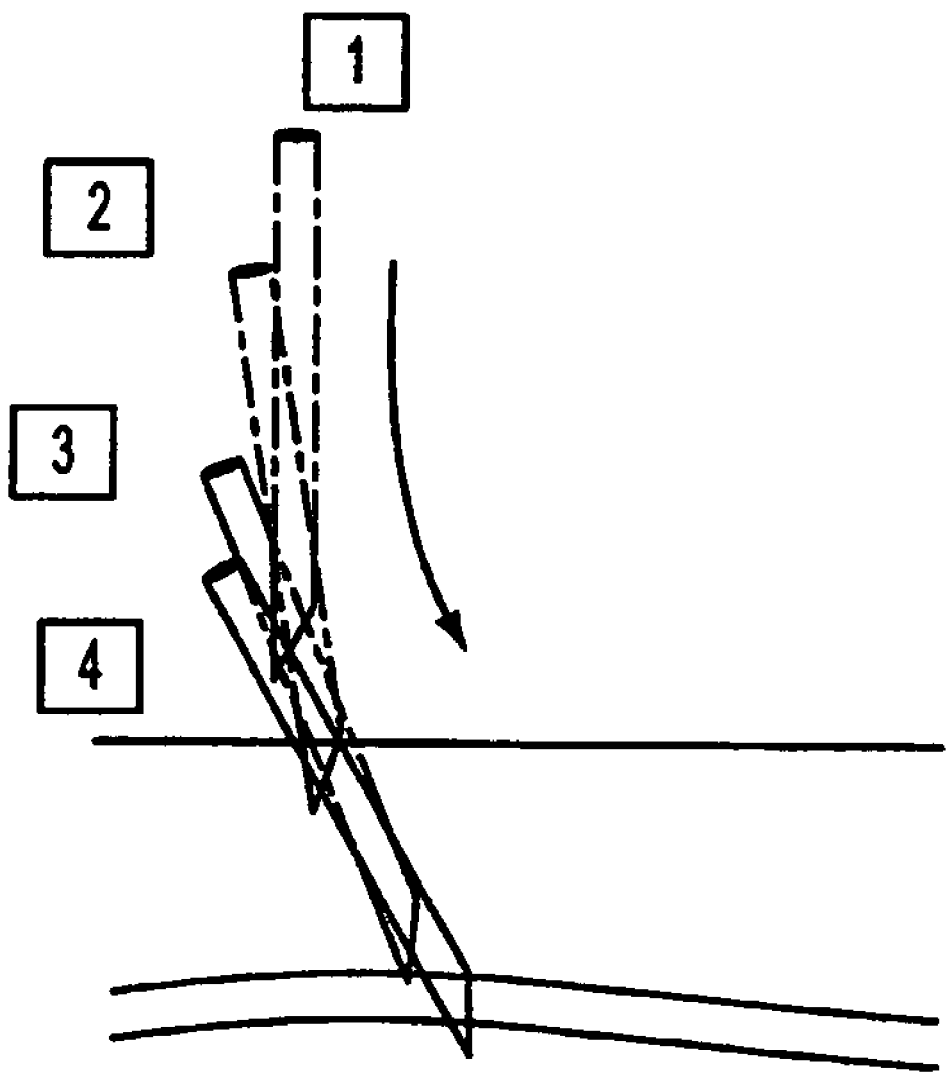
FIG. 15 is a pictorial diagram showing a straight microneedle with a non-rectilinear motion shown in four sequential positions in accordance with the invention.

As an alternative to a straight microneedle having an orthogonal entry, a curved microneedle can be used with orthogonal entry. See FIG. 12. In the alternative, a straight microneedle can be used with angled entry. See FIG. 13. In the alternative, a curved microneedle can be used with rotational entry. See FIG. 14. In the alternative, a straight microneedle can be used with a non-rectilinear motion. See FIG. 15. The alternate approach shown in FIG. 15 utilizes motion that does not match the shape of the microneedle. This results in the microneedle penetrating one layer of tissue with minimum disruption while producing more disruption at other depths. This effect can be used to minimize pain while still disrupting enough blood vessels to enable sufficient sample collection. FIG. 15 shows a straight microneedle with circular motion, steps 1 to 4, where the center of the motion is well above the surface of the skin. Other motion forms are anticipated including complex forms.

The microneedle is preferably extended and retracted mechanically. Microneedle extension and retraction can be powered by a single device or a combination of devices. For example, a DC motor can be used to drive an extending means and a spring can provide the return force. Alternatively, a powered source such as a DC motor can both drive the microneedle into and out from the skin. The later is a preferred approach in that it provides optimal control over the microneedle position.

Figure 22:
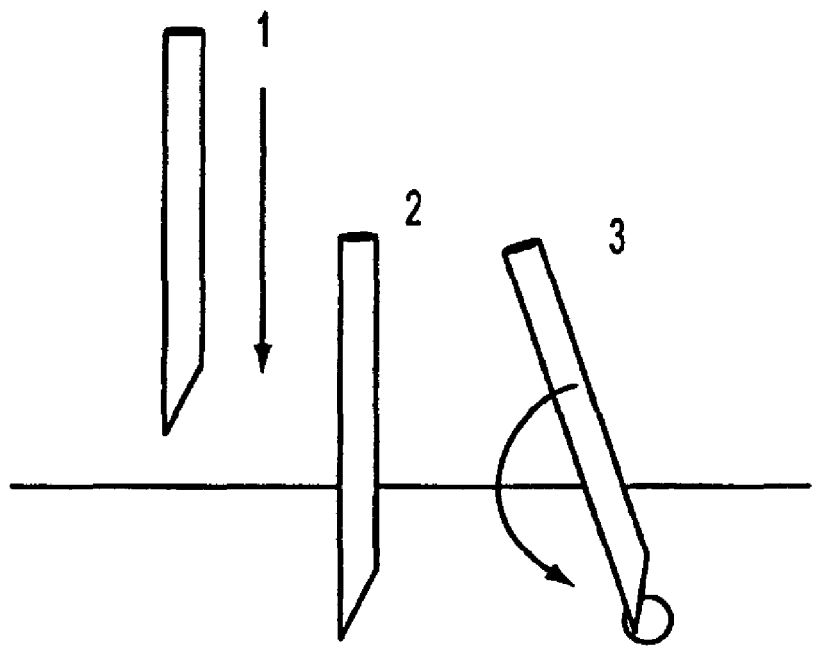
FIG. 22 is a pictorial diagram showing force applied to the proximal end of a microneedle to cause the distal portion to project into multiple directions in accordance with the invention.

The additional advantage of the articulated microneedle drive is that it mimics the exploratory motion of the mosquito. The microneedle can be driven to a maximal depth in one area and then, without removing it from the skin, reciprocate the microneedle and cause it to move in a new direction. In order to cause a new direction at a remote point on a penetrating microneedle, a stress must be imposed on the microneedle external to the skin while the distal end of the microneedle is still in the skin. See FIG. 22.

It is understood that various techniques can be used to drive the microneedles in accordance with the invention. Aside from the techniques discussed above, extending and retracting the microneedle can be accomplished using a microminiature DC motor and associated gear train. See e.g., FIG. 10. In this embodiment rotational output of the motor (not shown) is transferred through a gear train 492 to an internally threaded gear 494 located above the microneedle 414. The rotation of the gear causes a 'leadscrew' 490 to move linearly to gear rotation. Thus the motor causes a drive to extend or retract the microneedle 414. This design can achieve the penetration forces necessary, a value that is dependent on skin type, thickness and physical microneedle parameters, typically in the range of 0.01 to 0.07 Newtons.

Figure 10:
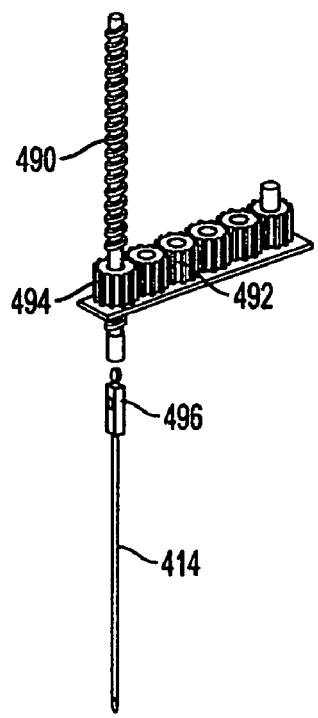
FIG. 10 is a pictorial diagram showing a lead-screw drive mechanism for microneedle motion in accordance with the invention.

The lead screw drive mechanism is preferably driven by a captured nut forcing the screw to travel co-linear with the intended microneedle travel. The lead screw engages with the microneedle assembly, pushes the microneedle into the tissue, pulls the microneedle out and disengages from coupling 496. The drive mechanism preferably pivots to engage the next microneedle assembly. The nut can be driven by gears as shown in FIG. 10, or a belt or other motion transfer mechanisms. The back end of the microneedle can be accessed by various techniques including but not limited to an opening in the engagement mechanism, an opening in the microneedle side or a bend in the microneedle exposing the proximal opening. Incorporation of a leadscrew mechanism suitable for use in conjunction with the invention based on the disclosure herein is well within the scope of one skilled in the art.

Other motion generating sources or motion conveyance can alternatively be used. For example, the motor can drive a cam device with features that cause the microneedle to extend downward with a predetermined rate profile. Cam features, or springs, can be used to retract the microneedle. Also, a shape memory alloy material (SMA) can be used to cause the microneedle to extend down and back. The heating and cooling of the SMA can cause the appropriate amount of force and displacement. A solenoid type device can be used to either drive the microneedle directly or index the microneedle. Such a device can be used like a motor.

Having articulated motion allows the microneedle to be extended into the skin incrementally to the correct depth. This invention is suitable for use on skin surfaces where a relatively flat surface is available equal to or larger than the areal dimension of a wrist. Although, the invention can be configured to acquire blood from more curving surfaces such as a finger. The invention is preferably configured to acquire blood from specific places such as the upper arm, wrist, abdomen, back, thigh or lower leg. The invention can be disposed or worn beneath clothing to render it inconspicuous.

Exemplary device configurations for differing body locations are discussed in more detail below. Depending on the location selected, the thickness of the skin surface and depth to the capillary bed is variable. For example, the epidermis varies in thickness from 0.02 mm at the eyelids to 1.4 mm on the soles of the feet. The dermis likewise varies from 0.6 to 2.5 mm. The invention is preferably configured to have a distal end of the microneedle reside into the vascular plexus but not go to a depth sufficient to penetrate the deep dermal vascular plexus. Accordingly, the invention preferably operates over a range of about 1.0 to 2.0-mm penetration into the skin surface.

Exemplary Sensor Structures

Figure 16:
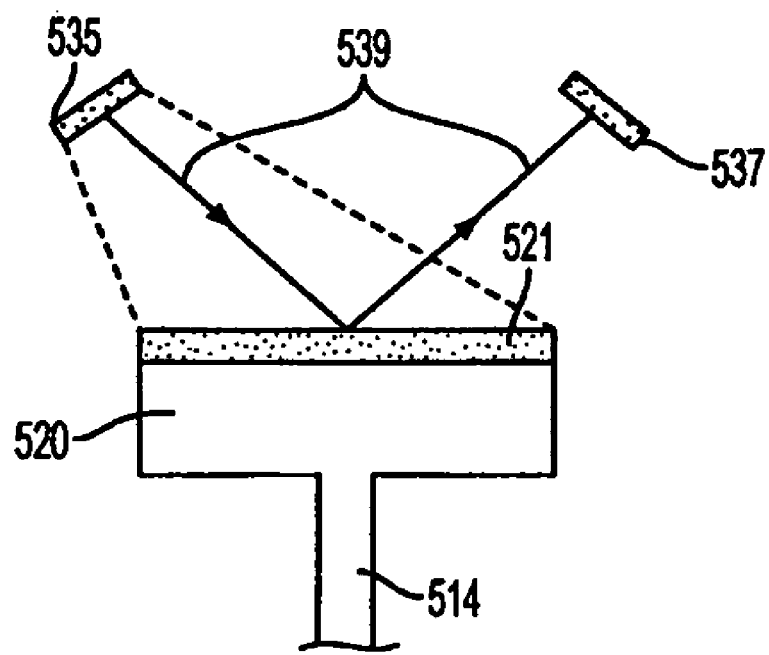
FIG. 16 is a pictorial diagram showing the basic configuration for improved sensitivity in accordance with the invention.
Figure 17A:
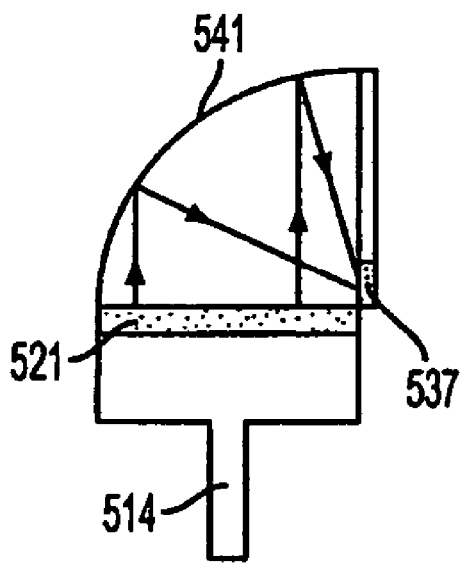
FIGS. 17a and 17b are pictorial diagrams showing an exemplary configuration for enhanced light collection using a spherical mirror to improve sensitivity in accordance with the invention.
Figure 17B:
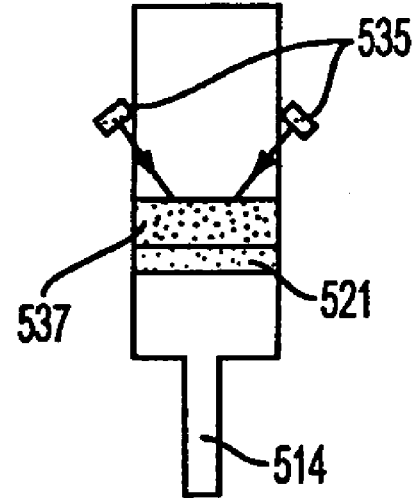

Various sensor structures are compatible with the invention. For example, optical detection can be achieved by techniques such as colorimetry and fluorescence. FIG. 16 shows basic configuration having a microchannel 520 and a reaction layer 521 in fluid communication with a microneedle 514. The reaction layer can be a membrane that is coated with a chemically active components that provide a change in color in the presence of the desired analyte (e.g., glucose) for colorimetric measurements. A fluid sample is collected via microneedle 514 and is stored in microchannel 520. The appropriate reagent is preferably contained within the microchannel 520 so that a reaction is initiated upon collection of the fluid sample. The sensor is disposed generally above the microchannel 520 and has an emitter 535 operable to illuminate the reaction layer with an appropriate frequency of light. The sensor also has a detector 537 operable to detect light reflected off of the reaction layer as shown by arrows 539. The detector 537 can be implemented using a photodiode with single or multiple picture elements (pixels). The example of such a device is a CMOS or CCD imager. The emitter and detector are preferably controlled by the processor (not shown). The detector output is preferable read by the processor and is further processed in order to determine the results of the reaction. FIGS. 17a and 17b show an enhanced collection configuration to improve sensitivity. This sensor configuration includes a spherical mirror 541 for reflecting light from one or more emitter 535 to the detector 537.

FIGS. 18a and 18b show alternative sensor configurations. FIG. 18a shows a microchannel 520 and a reaction layer 521 in fluid communication with a microneedle 514. Also shown in FIG. 18a is a cover 588 as discussed above. The reaction layer 521 can be a membrane or porous media that is coated with a chemically active component that changes color in the presence of the desired analyte (e.g., glucose) for calorimetric measurements. A fluid sample is collected via microneedle 514 and is stored in microchannel 520. The appropriate reagent is preferably contained within the microchannel 520 so that a reaction is initiated upon collection of the fluid sample. The sensor is disposed generally above the microchannel 520 and has an emitter 535 operable to illuminate the reaction layer with the appropriate frequency of light. The sensor also has a detector 537 operable to detect light reflected off of the reaction layer 521. Lenses 543 are disposed between the between the emitter 535 and the reaction layer 521 as well as between the detector 537 and the reaction layer 521. Lenses 535 generally focus the light for improved illumination of the reaction layer 521 and light collection at the detector 537. FIG. 18b is similar to FIG. 18a but includes a coupling prism 589 disposed on the cover to improve performance of the detector.

FIGS. 19a and 19b show further alternative sensor configurations. FIG. 19a shows a microchannel 520 and a reaction layer 523 in fluid communication with a microneedle 514. Also shown in FIG. 19a is a cover 588 as discussed above. The reaction layer 523 is shown as a generally thin layer having assay reagents mixed in a support matrix applied to the microchannel 520. A fluid sample is collected via microneedle 514 and is stored in microchannel 520. The appropriate reagent is preferably contained within the microchannel 520 so that a reaction is initiated upon collection of the fluid sample. The sensor is disposed generally above the microchannel 520 and has an emitter 535 operable to illuminate the reaction layer with the appropriate frequency of light. The sensor also has a detector 537 operable to detect light reflected off of the reaction layer 523. Lenses 543 are disposed between the between the emitter 535 and the reaction layer 523 as well as between the detector 537 and the reaction layer 523. Lenses 535 generally focus the light for improved illumination of the reaction layer 523 and light collection at the detector 537. FIG. 19b is similar to FIG. 18a but includes a coupling prism 589 disposed on the cover to improve performance of the detector. It is understood that the microchannel cover 588 can be enhanced with a variety of optical properties such as lenses, filters, reflective structures, refractive structures and the like without departing from the invention.

Enhanced Blood Collection

Figure 20A:
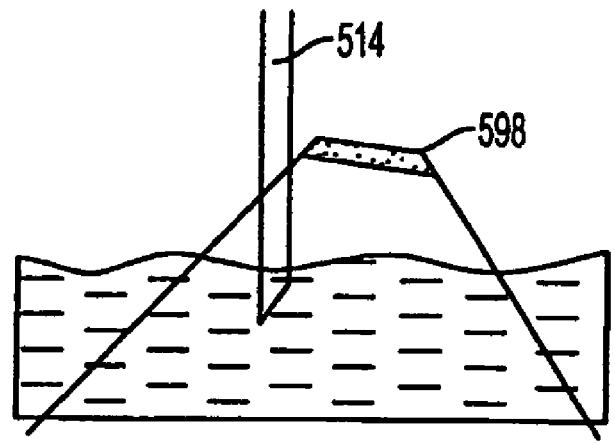
FIG. 20a is a pictorial diagram showing enhanced blood collection by localized heating of capillary structures (blood) near puncture site in accordance with the invention.
Figure 20B:
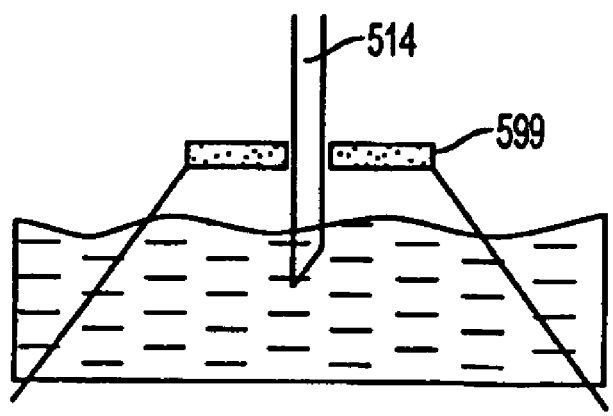
FIG. 20b is a pictorial diagram showing an alternative structure for enhanced blood collection by localized heating of capillary structures (blood) near puncture site in accordance with the invention

The invention also encompasses various techniques for enhanced blood collection. FIGS. 20a and 20b show the use of heating sources (e.g., infrared emitting LED) to heat the tissue near the collection site. Heating the capillary structure of the tissue at the collection site can lead to improve the blood supply and enhanced collection using microneedles. FIG. 20a shows an exemplary microneedle 514 inserted in skin or tissue. Heating source 598 is located to one side of the microneedle and is directed towards the tissue thereby heating the tissue in which the microneedle is inserted. FIG. 20b shows an alternate embodiment in which the heating source 599 is generally ring shaped and is located coaxially around the microneedle 514.

Automatic Detection of Blood

Figure 21:
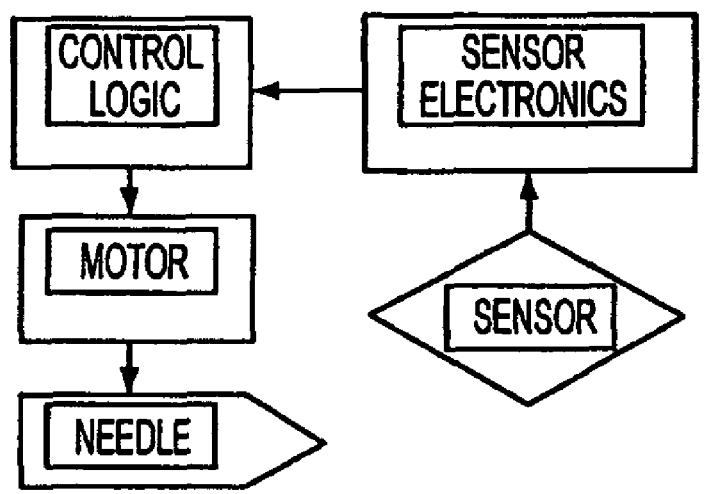
FIG. 21 is a block diagram showing a feedback loop from blood sensor to control logic to control the depth of microneedle penetration in accordance with the invention.

To simplify the acquisition of blood and to assure that an adequate sample is taken this invention encompasses the use of a blood detection sensor. The blood detection sensor provides control over the penetration and extraction control. The sensor feedback loop works by incrementally driving the microneedle into the skin, waiting an appropriate time for blood to fill the microneedle and sensor and then retracting the microneedle. See FIG. 21. If no blood is detected within a reasonable period of time, then the motor can further drive the microneedle to a greater depth. When blood has been acquired the microneedle is retracted.

The blood-sensor can be located at various points along the blood path (e.g., microneedle, microfluidic channel, microfluidic well or at the reaction site) of the test device or preferably, the test means itself is the sensor. The optical sensor for the colorimetric test can detect the appearance of blood, prior to making a reading to ascertain the glucose level. This provides dual function of the sensing device and provides a feedback loop without additional cost. Alternatively, a capacitance, conduction or resistive sensor can be used in the microfluidic channel or well to determine when liquid is present.

Since the depth and rate at which blood is acquired are site, user and time specific there is need to have these variables stored in the system. Since it is envisioned that this device be used with a cartridge containing a multiplicity of microneedles, and since each blood acquisition is a repetitive search and detect methodology, it is helpful to the user if the system could optimize itself to achieve minimal blood acquisition time.

Analyte Testing and Delivery of Pharmaceutical Agents

Since 1987, the American Diabetes Association (ADA) has provided criteria for the statistical assessment of self-monitoring blood glucose (SMBG) meters. In 1987, the ADA recommended blood glucose measurements should be within 15% of the reference and that future SMBG meters should have less than 10% variability. By 1993, it was evident new technologies, at this time, were not achieving the 1987 goals. However, in 1996, the ADA recommended less than 5% variability for future SMBG meters.

In comparison to this standard, recent evaluation of the relative accuracy of selected, available SMBG meters, representing visual, colorimetric and amperometric detection, showed that current products vary from a reference by approximately −5 to +20%. The significance of statistical errors for SMBG meters depends on clinical assessment, that is, whether the error results in inappropriate clinical management.

Recognizing that SMBG meters using relatively large microliter volumes of blood show large statistical errors. The invention contemplates the use of small (e.g., nanoliter) volumes for samples. This helps to achieve the small size of the device necessary for ambulatory monitoring. The requirement of new design and precision manufacturing approaches, as noted, are the subject of this invention, i.e., to achieving better accuracy. The invention contemplates the use of small (e.g., nanoliter) volumes for samples. In addition to achieving better accuracy, this also helps to achieve the small size of the device necessary for ambulatory monitoring. The requirement of new design and precision manufacturing approaches, as noted, are the subject of this invention.

In order to support small volume fluid assays, the invention incorporates microfluidic channels with a reagent membrane for a plurality of blood analyte testing. FIG. 3 shows an exemplary array of microchannels 20 each with precise dimensions, that is, micrometer dimension tolerances. A membrane can be bonded onto the array to prevent the migration of red blood cells, but not liquid blood constituents. The unbonded side of the membrane is preferably coated with assay reagents either uniformly or in spatial defined locations, that is, the channel locations. When blood enters an individual microchannel, the dimension of the microchannel determines the volume. This is critical to the precision of the assay, that is, filling the microchannel provides the analytical volume for assay. Subsequent to filling, the blood constituents migrate through the "reaction layer" (e.g., a polymer) and initiate, by wetting, the assay chemistries within the reaction layer as discussed herein.

The polymer for the reaction layer, may be any commercial polymer suitable for the desired assay whereby, by wetting, the assay chemistries may be initiated within or on the other side of the polymer layer. Preferred polymers include hydroxyethyl cellulose, sodium alginate and gelatin. The reaction layer is preferably cast on polymers such as styrene or any polymer of high liquid transmittance and capability for sealing. The polymer and reaction layer is preferably sealed to the capillary well using a device with precision dimensions to surface bond the polymer and reaction layer using adhesive bonding by heat, adhesive materials or other means or agents.

Figure 23:
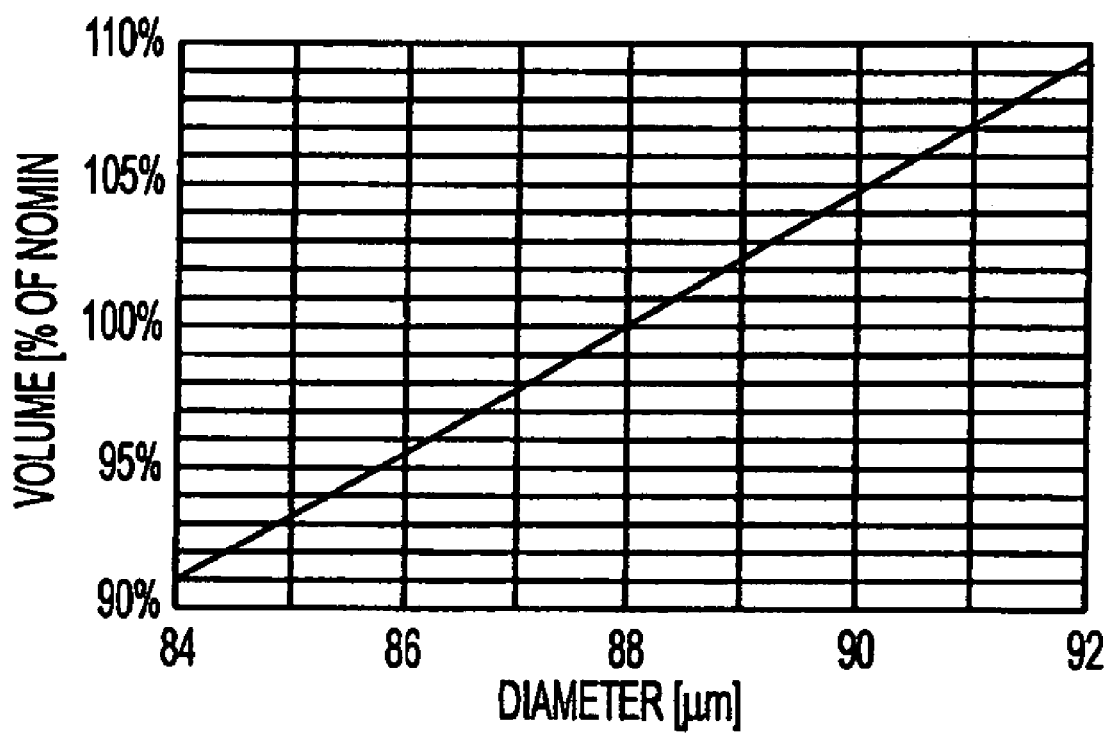
FIG. 23 is a graph showing the error in the volume of a 1 cm length of a nominal 88 micrometer tube by increased tube diameter.

The need for precision in the dimension of the device is evident from FIG. 23. This figure shows the error in the volume of a 1 cm length of a nominal 88 micrometer tube when the tube diameter is increased (e.g., a 5% error occurs with a nominal 91 micrometer diameter tube). It can be seen that a change in diameter of less than 3 micrometers in a nominal 88 micrometer diameter tube can result in an approximately 5% error in volume. Accordingly, the tolerance required to control volume to less than 5% is on the order of <3 micrometers.

The assay chemistries can be based on widely used techniques such as the Trinder reaction. The Trinder reaction is based on a coupling reaction between two dye precursors, viz.,

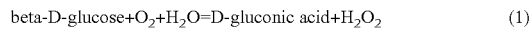

$$\text{beta-D-glucose} + O_2 + H_2O = \text{D-gluconic acid} + H_2O_2 \qquad (1)$$

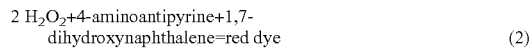

$$2\,H_2O_2 + \text{4-aminoantipyrine} + \text{1,7-dihydroxynaphthalene} = \text{red dye} \qquad (2)$$

in the presence of glucose oxidase for the first reaction and in the presence of a peroxidase for the second reaction. The Trinder reaction is widely used for glucose assays. The important features of the Trinder reaction are the long history of use, the stability of the dye precursors with elevated temperatures and the availability, and thermal stability, of the enzymes. The 1,7-dihydroxynaphthalene is soluble only in alcohol and a water soluble aromatic is preferred. This aromatic is preferably one of the water soluble reagents identified in U.S. Pat. No. 4,350,762—DeLuca, et al., for example, the sodium salt of 2,4-dichlorophenyl sulphonate.

The specific configuration of the invention differs from prior technology in a number of ways including but not limited to the examples discussed below. The invention incorporates micromachined, or micromolded, microchannels with precise dimensions, that is, micrometer dimension tolerances. The accumulation or delivery of fluid (e.g., blood, pharmaceutical agent . . . ) is direct, that is from a microneedle. The accumulation of fluid in the microchannel is entirely dependent on capillary forces. The microchannel surfaces may be thinly coated with insoluble materials, such as various polymers, to enhance the capillary forces and minimize blood coagulation. The microchannels can be fabricated as an array in large number, e.g., 150 on a 1.5" diameter. The microchannels can be dimensioned for minimal fluid volumes (e.g., 100-500 nanoliters of fluid or less).

The microchannels can be provided with a mechanism to detect when the fluid completely fills the device such that use of the associated microneedle can be terminated (i.e., the microneedle can be retracted), as discussed below. The microchannels and assay chemistries may be applied to assays for analytes other than glucose. The invention can be modified to provide multiple channels for multiple assays using a single blood sample. So called "calibration microchannels" may be initially filled with calibration fluid and the assay initiated for calibration purposes as discussed in more detail below. This aspect of the invention can only be realized with the structures disclosed herein as discussed in more detail below. The microchannels may be filled with drug and used to deliver drugs used in small doses (high potency). The capability to deliver drug and or monitor blood analytes in an automated fashion using a portable device can only be realized with the structures disclosed herein.

Ultimately, the invention encompasses the combination of both the monitoring and pharmaceutical agent delivery system within one unit (preferably a disposable unit). For example, military personnel may be unknowingly exposed to a toxin. The device can periodically extract blood and assay for predetermined toxins. If a toxin is detected, the device can deliver antidote.

Self Calibration

In order to increase the accuracy of an enzymatic test, it has been found helpful in current SMBG meters to provide, with each batch of test strips, a calibration factor that is a correction factor to be used to more accurately determine the correct result. Two calibrations are needed—one to compensate for instrument components and secondly to compensate for the particular sensitivity of a specific batch of chemical components. Various techniques have been developed to achieve this in an automated fashion.

The invention preferably incorporates autonomous self-calibration functions so that no user actions are required. One or more calibration microneedles (i.e., associated with a calibration microchannels) are preferably incorporated in the microfluidic structure. When the calibration microneedle is actuated, it is pushed down but no microneedle extends from the disposable unit. In the fully extended position, the unit releases a calibration fluid into the microfluidic channel. For example, in the extended position the calibration fluid travels through the conduit and fills the microchannel. The assay system provides a measure of the glucose in the calibration solution and compares this measure value with the known value. Preferably, a correction factor is derived from the calibration process. The correction factor is preferably stored electronically and is utilized during subsequent analyte testing.

A plurality of calibration microneedles can be used to compensate for any change in reagent or instrument properties. Thus the first measurement taken with the insertion of a new Disposable is to calibrate the meter. Subsequent measures are made on a timed basis and are used by the system software to compensate for change in reagent properties at room temperature.

Testing for Other than Glucose

The invention can be utilized to test for a variety of constituents including but not limited to enzymes, antibodies, alcohol level and other blood constituents. The invention can be designed to also incorporate HbA1c (glycosylated hemoglobin) blood testing, which is a test diabetics should have done about twice a year or more and provides a measure of long term effectiveness in regulating blood glucose levels. Virtually any blood test that has chemistries that can be used at or near body temperature can be incorporated within this system. It is also envisioned that the invention can provide Polymerase Chain Reaction (PCR) testing to genetically identify foreign bodies within the blood. A relatively small heating element can be provided for testing that utilizes heat melts of duplex nucleic acid. Insulation can also be provided to minimize any heating of surrounding structure.

4. Alternate Assay Technologies

A review of the literature shows, by select examples, that a variety of calorimetric, electrochemical and fluorescent assay methods are available. Of these methods, U.S. Pat. No. 6,118,126—Zanzucchi discloses fluorescence assay techniques and this technology may be used as an alternate method of assay for the device of this invention. This technology allows for the enhancement of fluorescence from textured surfaces. In connection with the invention, enhanced fluorescence can provide improved sensitivity for the assay of small samples. It is understood that a variety of other assay techniques can be used without departing from the scope of the invention.

Use of a Neural Network to Optimize the Acquisition of Blood

In order to make the system more user friendly, a simple learning algorithm, using artificial intelligence (AI) schemes such as neural networks, can be used by the system's computer. The algorithm can infer from historical data of multiple blood acquisitions the parameters that are specific to an individual. These additional variables can be; location on the body, time from last meal, time since last exercise and time of day (capillaries are more blood rich during the day and particularly during times of physical activity). These data can then be used to infer the probability of blood acquisition and therefore the optimal microneedle depth and dwell time.

Since physical activity is closely related to the metabolism of glucose in the body, this invention also encompasses the inclusion of an accelerometer within the ambulatory device. Both the accumulative motion and time since last physical activity can provide critical data to assist in the predictive ability. Software, such as the "Recommender" may also be included in this invention. See FIG. 26. This software can provide the user better recommendations as to how to control their glucose with drug or dietary regiments, e.g., in the case of type 2, or noninsulin dependent, diabetes.

The invention is preferably operable to be linked to an external computing device such as a PDA. Preferably, the PDA can also store in memory the schedule of the person as additional information with respect to activity. This additional information may be used with the software to anticipate fluctuations of glucose in the user and to support recommendations on diabetes control.

Drug Modification

One of the major reasons for noncompliance is that there is not a tight feedback loop between the glucose measurement and compensatory actions. The invention can provide not only a reading of glucose level but recommendations for more or less insulin, or oral medication or nutritional supplements.

Often critical is insulin use. All people with Type 1 diabetes need to use it. Many people with type 2 or gestational diabetes also use insulin for good control. For Type 1 diabetics taking insulin injections, the need is to inject the appropriate mix of rapid or short acting insulin (lispro) and intermediate or long acting insulin (Lente or Ultralente). ADA recommends about four injections a day. If on an insulin pump, the need is to achieve a basal delivery to maintain fasting glucose levels and anticipate the need for bolus injections before meals. The invention can be coupled to either regiment and make the decision and estimating process easier.

Diet and Nutrition Modification

Automated diabetes management software has previously been developed to assist diabetics to control blood glucose levels—most have failed due to the complexity of the model and the unmet need for more glucose readings. Diabetic management software attempts to recommend changes to a diabetic's drug dosage or dietary regiment to minimize the occurrence of hyperglycemic or hypoglycemic events. These systems require extensive historical and real time data to accurately predict how an individual's blood glucose will behave with some level of intervention. Unfortunately, these systems have failed because user's behavior and physiological response is too unpredictable—only short term predictions based on real time blood glucose measurements can be used to help modify outcome.

Figure 25:
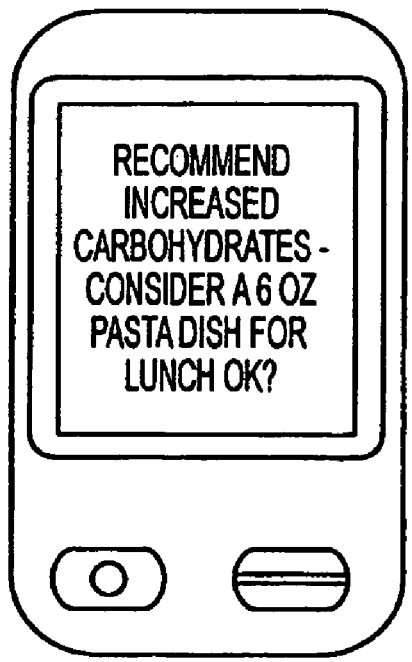
FIG. 25 is a pictorial diagram showing an exemplary PDA display showing dietary recommendations in accordance with the invention.
Figure 26:
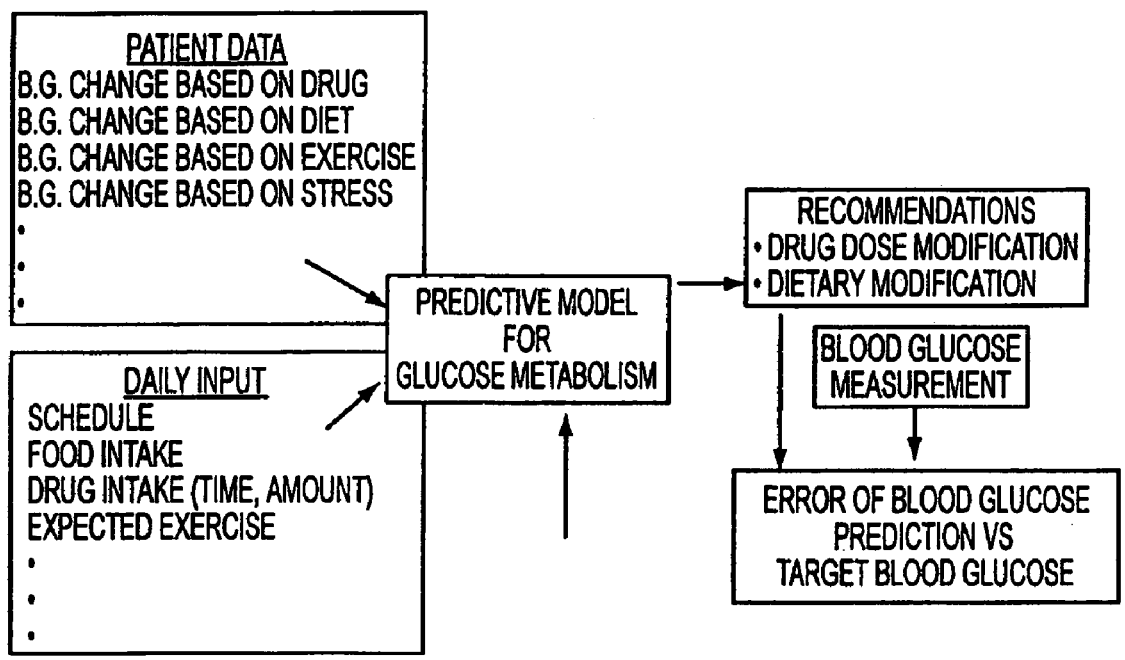
FIG. 26 is a pictorial diagram showing how data is entered into a Recommender System in accordance with the invention.

FIG. 25 shows an exemplary PDA display showing dietary recommendations. FIG. 26 shows pictorially how data are typically entered into a Recommender System. Since mathematical modeling of any biological system becomes difficult due to the numerous metabolic mechanisms, researchers have investigated the use of artificial intelligence (AI) including neural networks, fuzzy logic and expert systems.

Incorporation of an Alarm in the System

Since the invention is to be worn in a discrete place, it would be inconvenient for the user to have to physically or visually access it while wearing it to determine a glucose measure. It should also not be necessary for the user to be constantly interrogating the PDA to determine if the user's glucose is exceeding a predefine level, or has gone below a lower predefined level. It is more convenient, ergonomic and socially acceptable to use a wireless personal digital assistant, such as that produced by Palm or Handspring, that is modified to communicate directly with the Reusable unit.

Therefore it is envisioned with this invention that the wearable component or Reusable include an alarm to alert the user that their glucose reading is outside some predefined range. The alarm can be of the audible or vibration mode as commonly found in pager type devices. The invention is to the software to monitor the data and provide the alarm.

Timing System to Allow Flexible Predefined Testing Times

A timing system is preferably incorporated in the system software to provide for a flexible testing schedule. As discussed above, the user can program the times when their glucose test are to be taken and for setting the upper and lower limits for alerting the user. Whenever the user makes changes and with verification from the user, the information is preferably wirelessly downloaded to the system. During the day the user will not need to use the PDA unless alerted by the system to check for a glucose reading. The user can initiate a test from the PDA if wanting to make an immediate measurement. Once the user selects this command, verifies it, and transmits it to the Reusable, a confirmation is made back to the PDA.

Alternative Forms for Locating the Device on the Body

Figure 28:
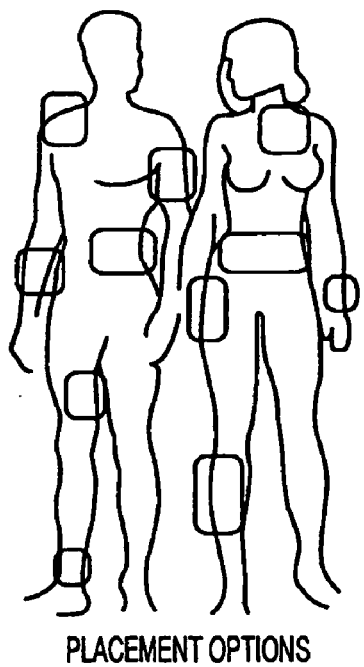
FIG. 28 is a pictorial diagram showing exemplary locations on the body for placement of a device in accordance with the invention.

The invention includes the ability to locate the device at various regions on the body. FIG. 28 is a pictorial diagram showing exemplary locations on the body for placement of a device in accordance with the invention.

Figure 29A:
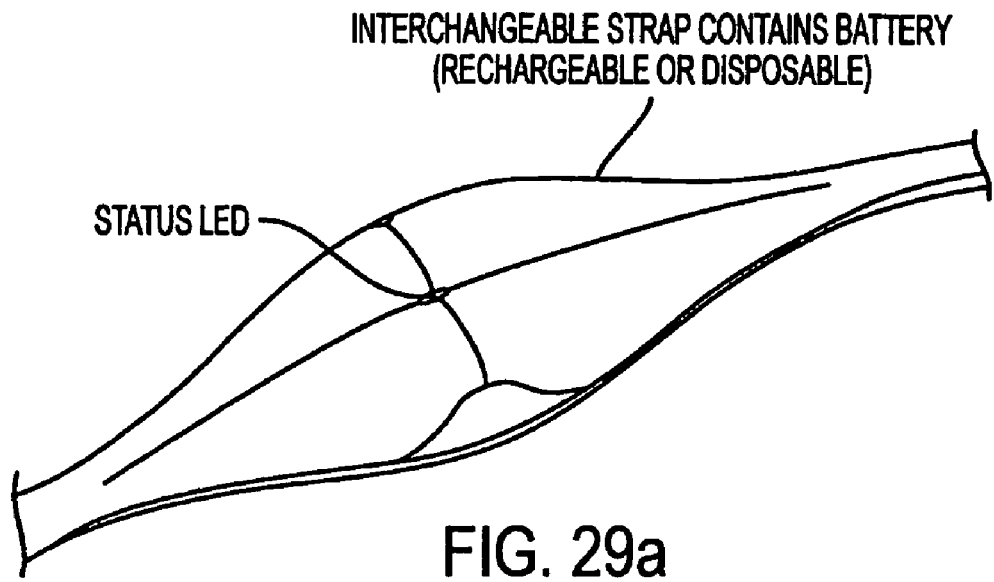
FIGS. 29a-29c are pictorial diagrams showing an exemplary embodiment suitable for location on the wrist.
Figure 29B:
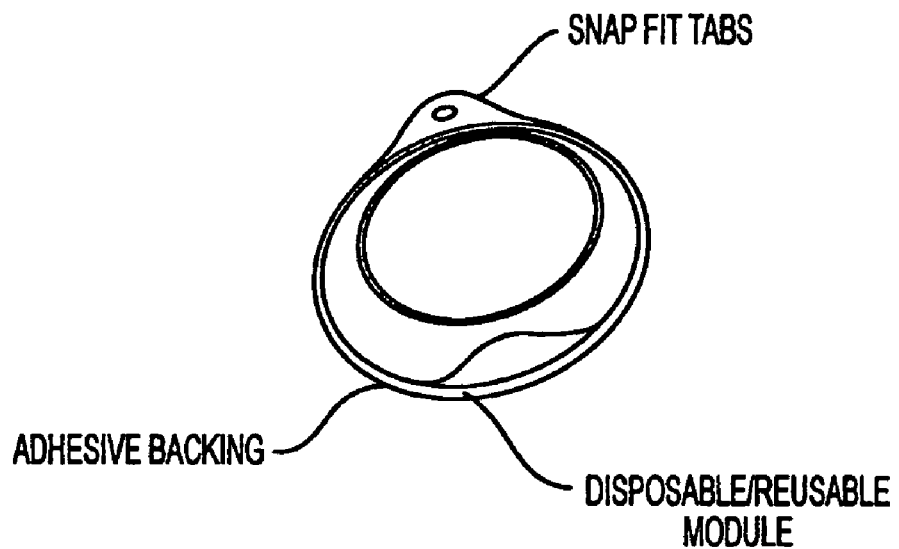
Figure 29C:

FIGS. 29a-29c are pictorial diagrams showing an exemplary embodiment suitable for location on the wrist. This configuration includes a strap optionally containing a battery that binds the disposable/reusable module to the wrist similar to a wrist watch.

Figure 30A:
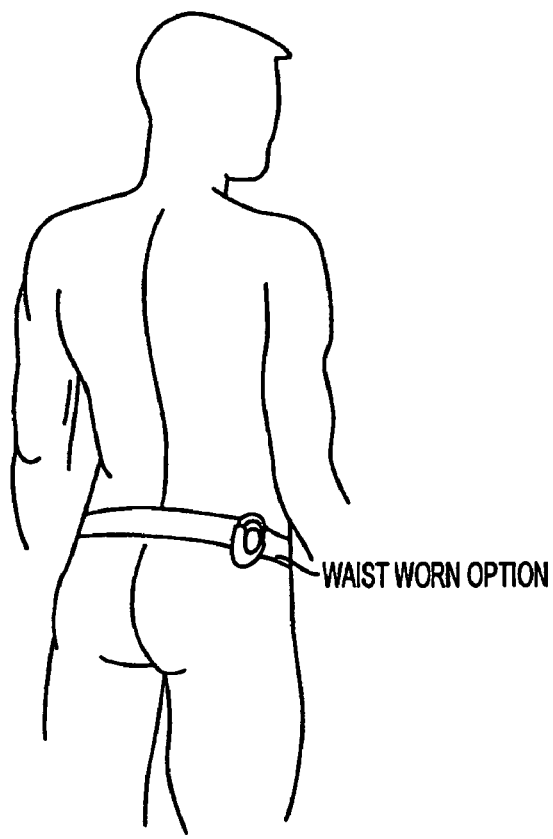
FIGS. 30a-30b are pictorial diagrams showing an exemplary embodiment suitable for location on the waist.
Figure 30B:
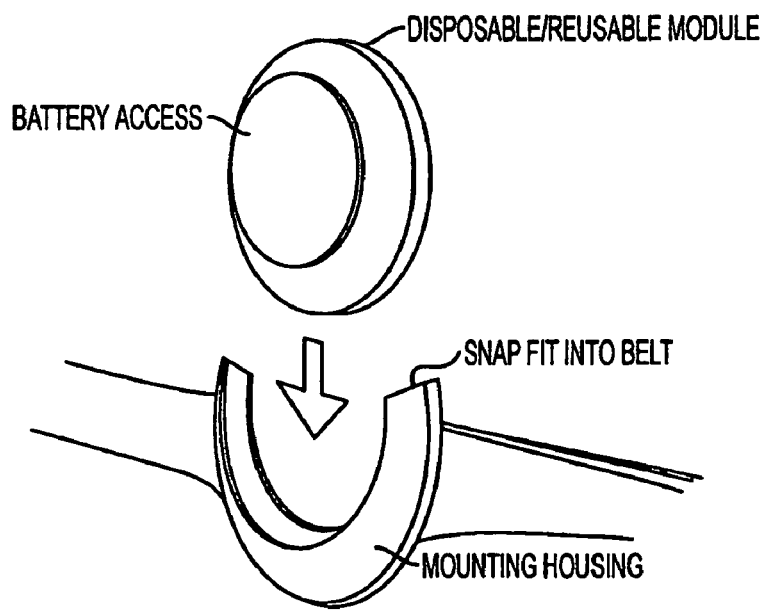
Figure 31A:
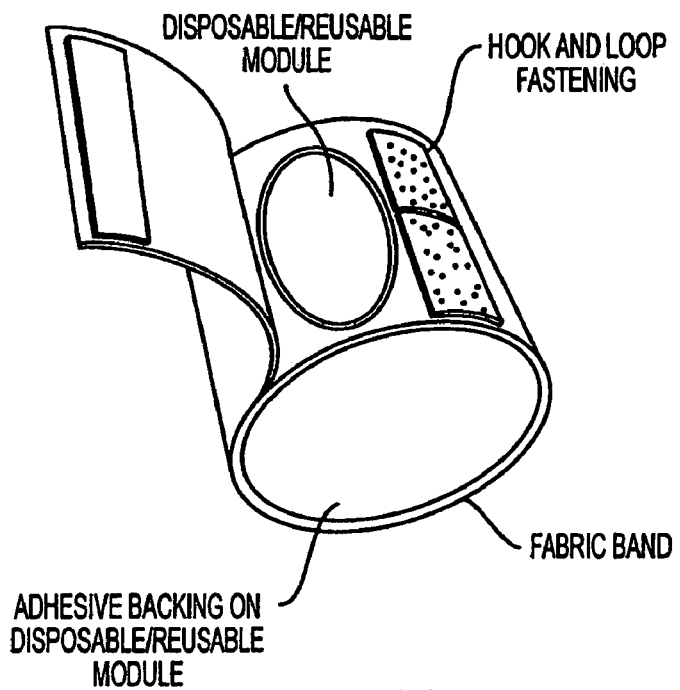
FIGS. 31a-31b are pictorial diagrams showing an exemplary embodiment suitable for location on the arm.
Figure 31B:
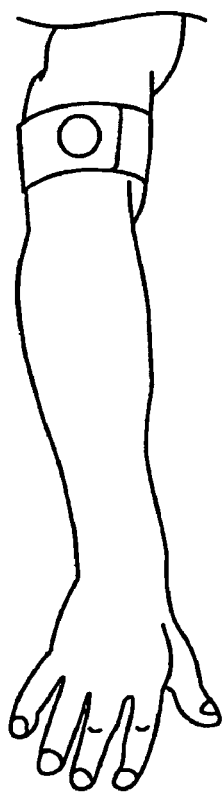

FIGS. 30a-30b are pictorial diagrams showing an exemplary embodiment suitable for location on the waist. This configuration includes a mounting housing with associated straps operable to hold the disposable/reusable module against the waist. FIGS. 31a-31b are pictorial diagrams showing an exemplary embodiment suitable for location on the arm. This configuration includes an arm band optionally fitted with hook and loop fasteners for attaching to the arm similar to a blood pressure cuff.

Figure 32A:
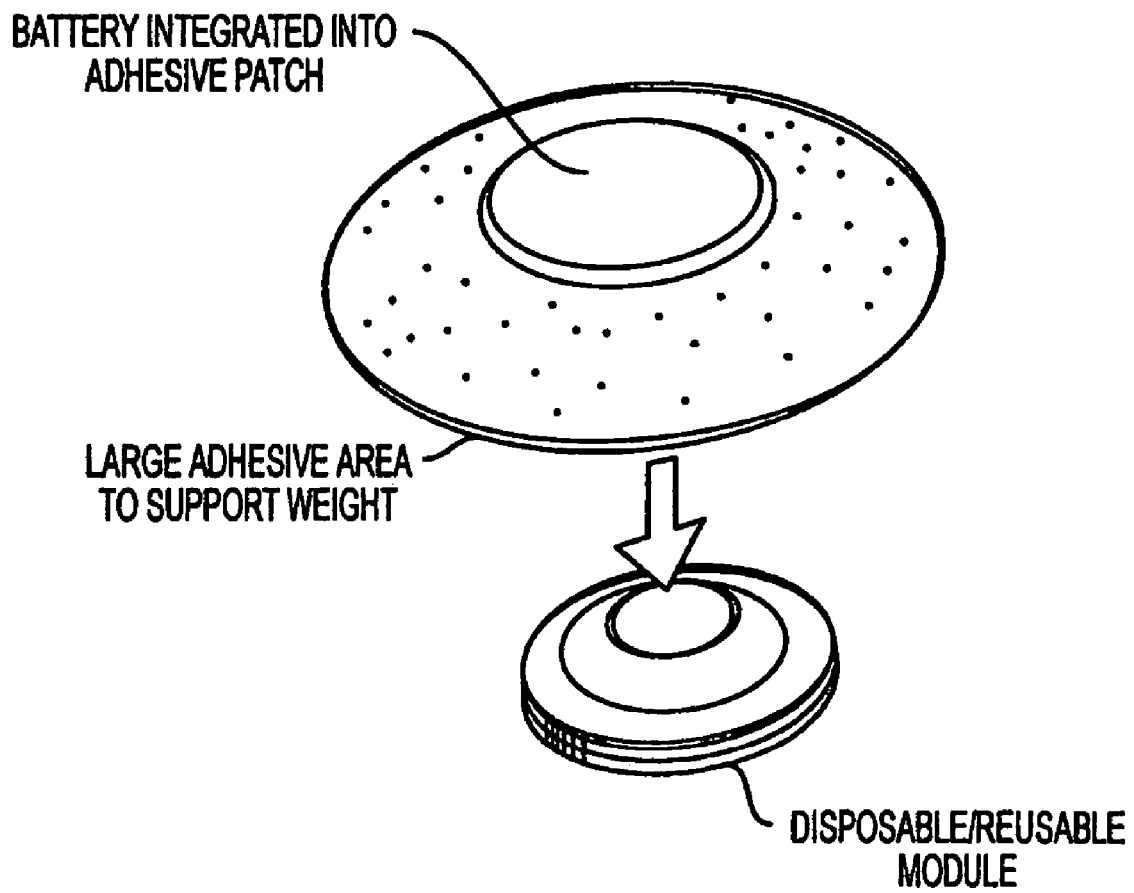
FIGS. 32a-32b are pictorial diagrams showing an exemplary embodiment suitable for adhesive mounting in a variety of locations including the leg.
Figure 32B:
Figure 33A:
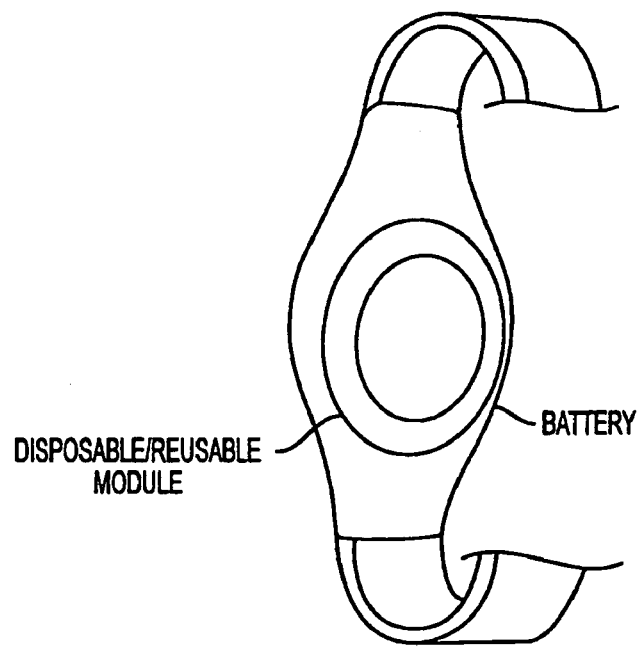
FIGS. 33a-33c are pictorial diagrams showing an exemplary embodiment suitable for strap mounting a device in accordance with the invention to the leg.
Figure 33B:
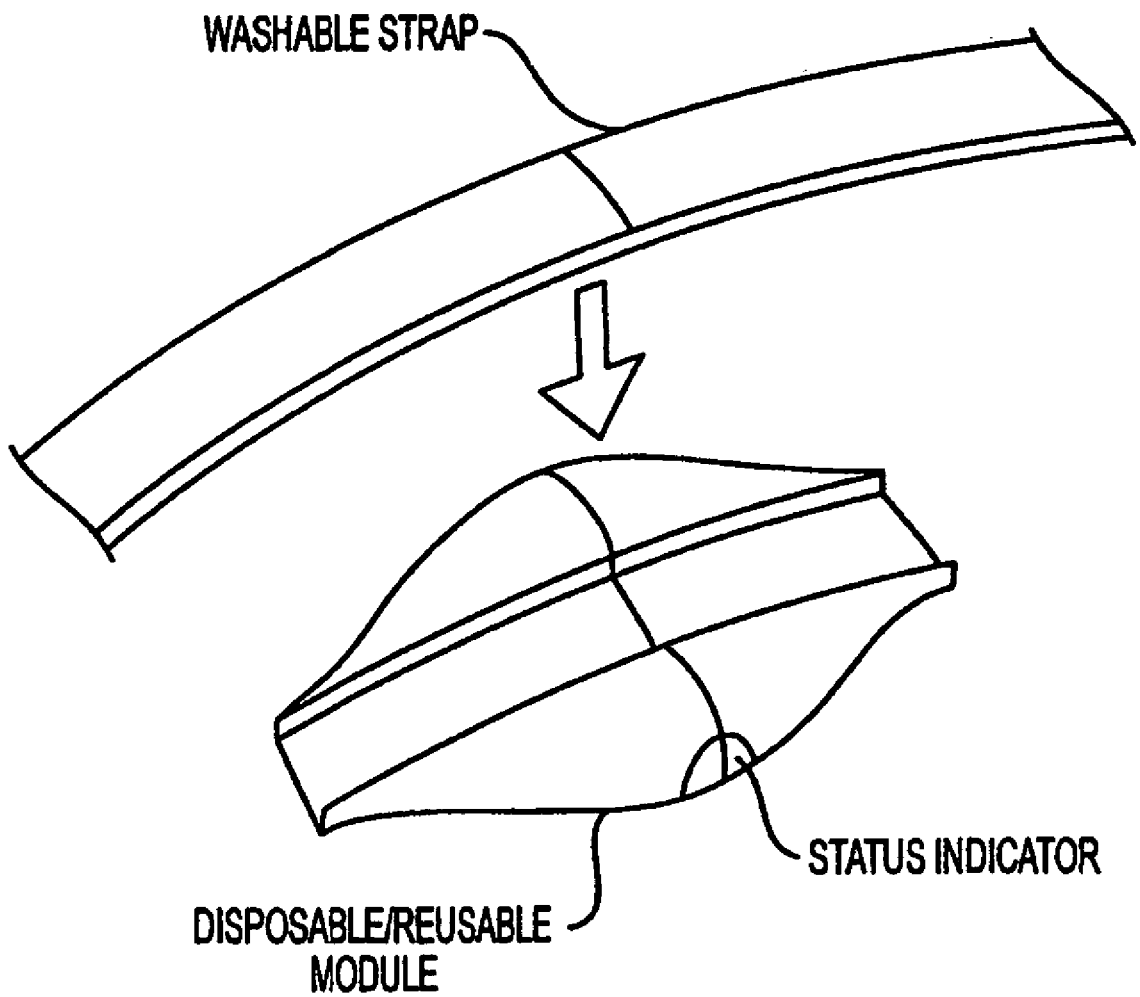
Figure 33C:
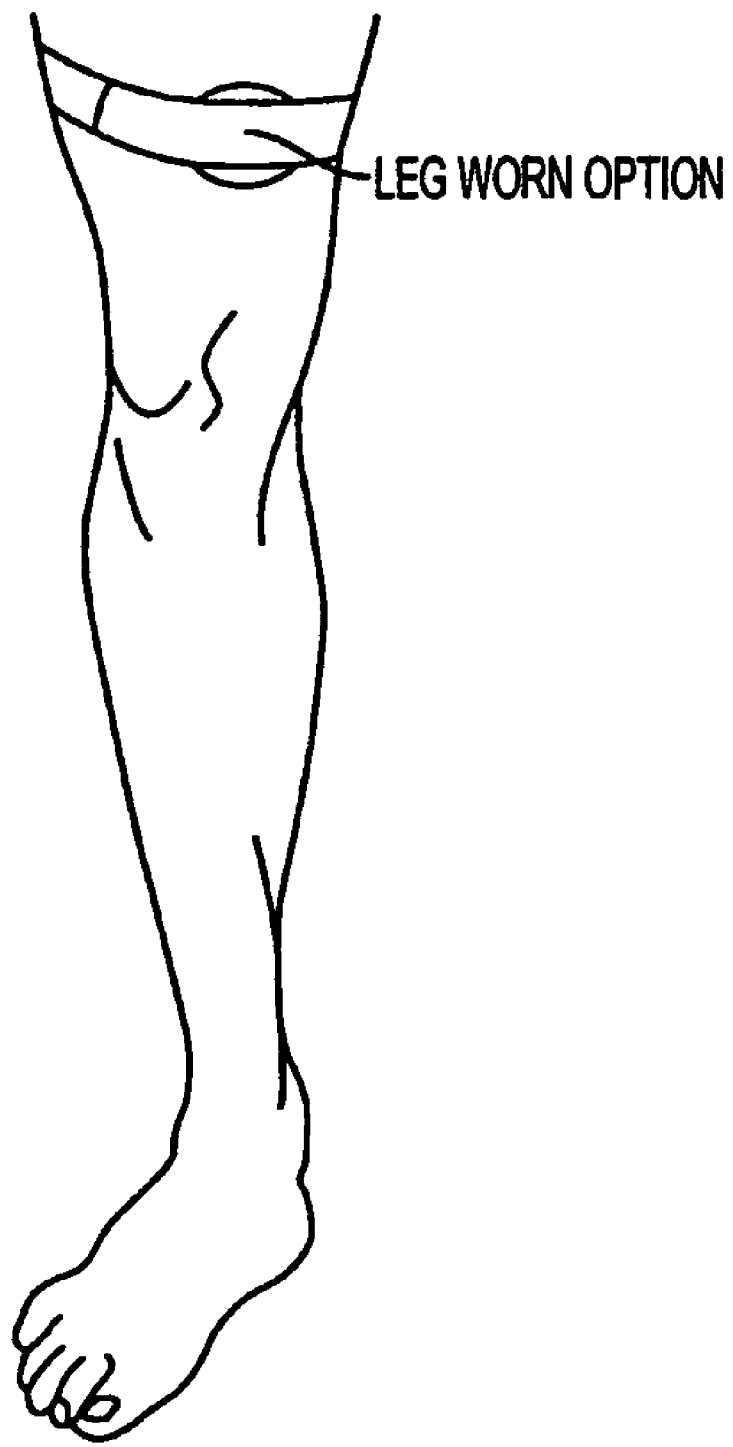

FIGS. 32a-32b are pictorial diagrams showing an exemplary embodiment suitable for adhesive mounting in a variety of locations including the leg. This configuration includes an adhesive backed disk that covers the disposable/reusable module, holding against the skin. FIGS. 33a-33c are pictorial diagrams showing an exemplary embodiment suitable for strap mounting a device in accordance with the invention to the leg. This configuration includes a mounting housing with associated straps operable to hold the disposable/reusable module against the leg.

Figure 34A:
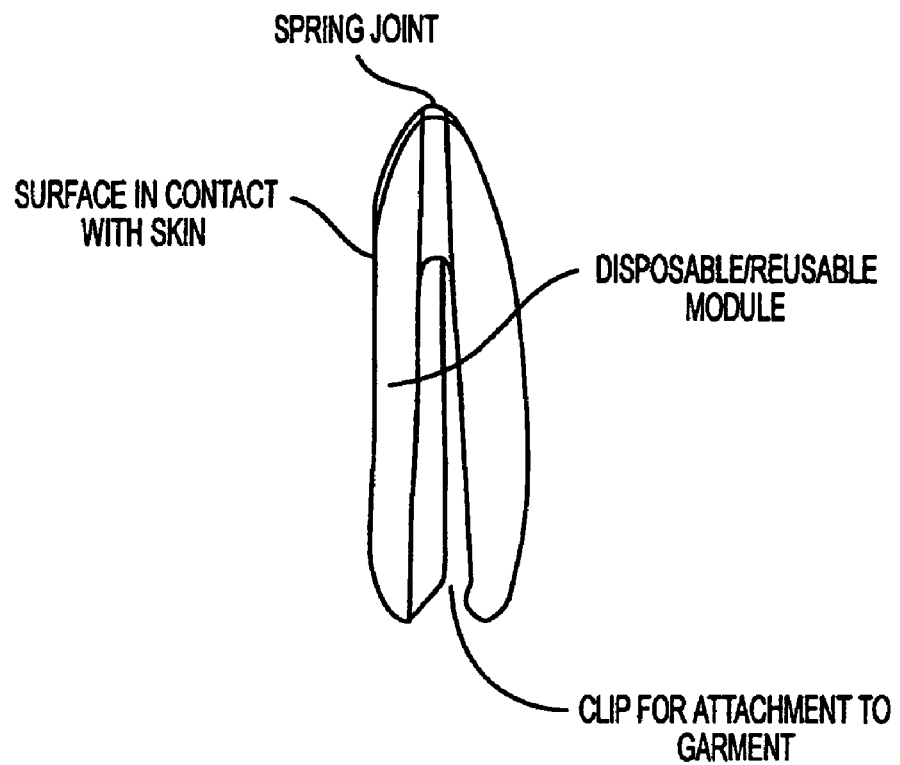
FIGS. 34a-34c are pictorial diagrams showing an exemplary embodiment suitable for clip and/or adhesive mounting a device in accordance with the invention to the waist via an undergarment.
Figure 34B:
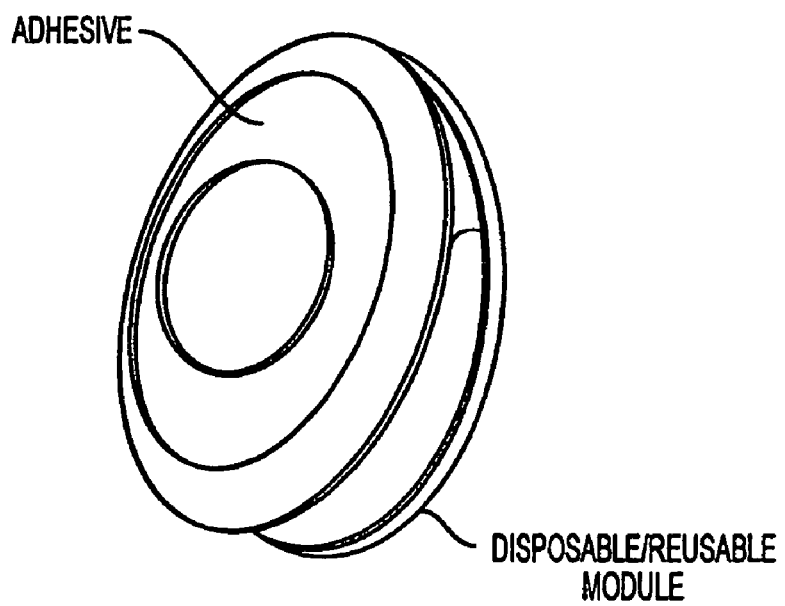
Figure 34C:
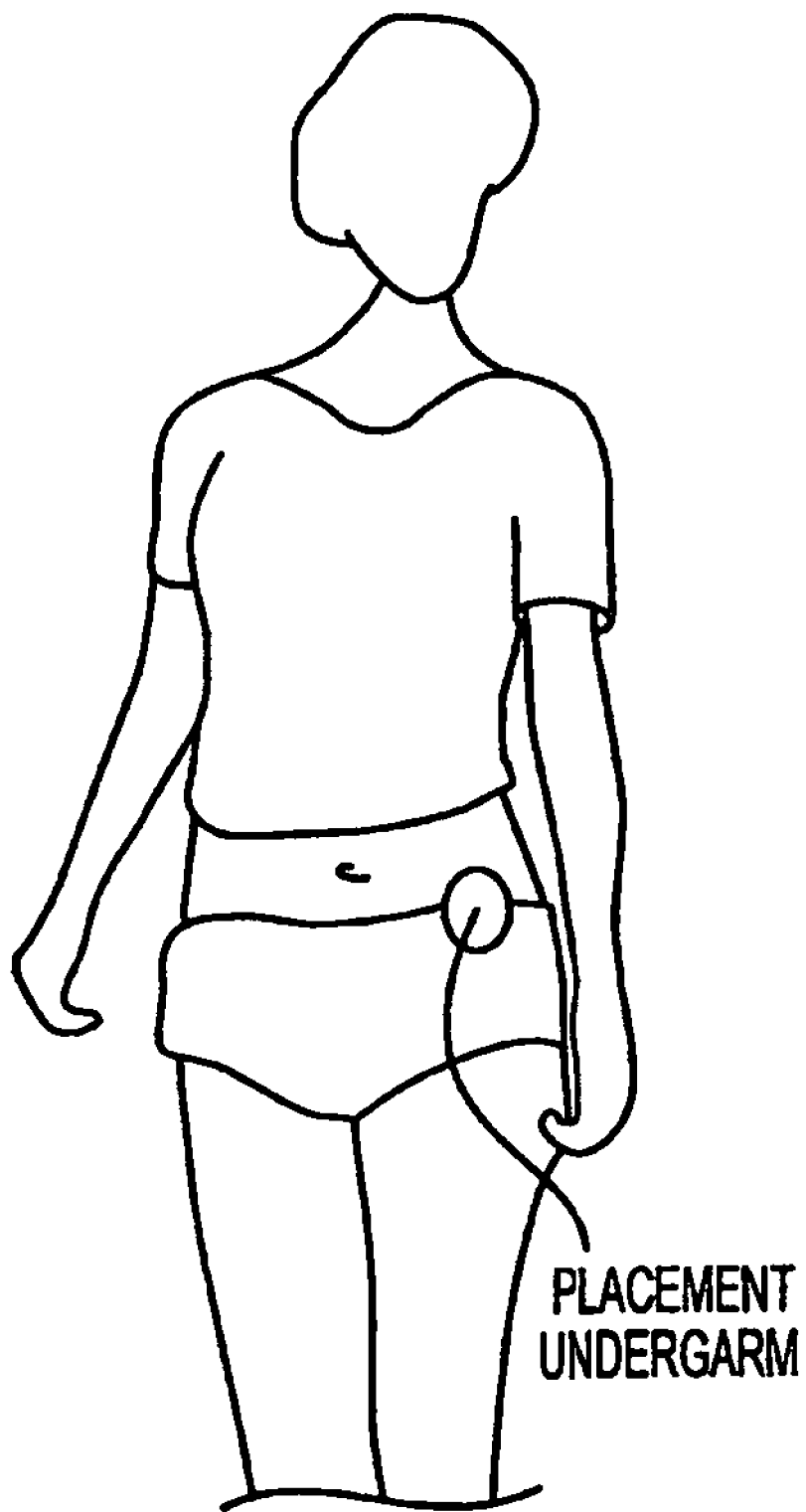

FIGS. 34a-34c are pictorial diagrams showing an exemplary embodiment suitable for clip and/or adhesive mounting a device in accordance with the invention to the waist via an undergarment. This configuration includes a mounting housing operable to hold disposable/reusable module and formed with a spring joint similar to a clothes pin. The disposable/reusable module is at least partially covered with an adhesive. The spring joint is placed over the edge of an undergarment and the adhesive is pressed against the skin (e.g. along the waist). It is understood that various other configurations are possible without departing from the scope of the invention.

While this invention has been described with an emphasis upon preferred embodiments, it will be obvious to those of ordinary skill in the art that variations in the preferred devices and methods may be used and that it is intended that the invention may be practiced otherwise than as specifically described herein.

What is claimed is:

1. An analyte monitoring device operable to draw a fluid sample from a subject, the device comprising:
    a plurality of microneedles disposed on a carrier,
    a plurality of microchannels defined as openings in said carrier, wherein each of the plurality of microneedles is at least intermittently in fluid communication with a corresponding microchannel, wherein each of the plurality of microneedles is connected to and moveable with a corresponding fluidic capture site and is constructed and arranged to collect the fluid sample from the subject, wherein the corresponding fluidic capture site is configured to fluidly couple to and deliver the fluid sample to at least one of the plurality of microchannels, and wherein each microchannel is associated with a reagent, at least one actuator operable to extend each microneedle and corresponding fluidic capture site to collect the fluid sample from the subject and to deliver the fluid sample to the at least one of the plurality of microchannels, and a controller operable to initiate analyte testing of the fluid sample.

2. The device of claim 1 wherein each of the first plurality of microneedles has an internal diameter in the range of about 25 to 200 micrometers.

3. The device of claim 1 wherein each of the first plurality of microneedles is fabricated from at least one of metal, plastic, glass and crystal.

4. The device of claim 1 wherein each of the first plurality of microneedles has a distal end that is operable to penetrate into a skin surface to a maximum of about 2.5 mm.

5. The device of claim 1 wherein the fluid sample is substantially blood.

6. The device of claim 1 wherein each of the first plurality of microneedles is at least intermittently in fluid communication with a microchannel via a conduit.

7. The device of claim 1 wherein each microchannel is operable to store the fluid sample and accumulation of the fluid sample in the microchannel is entirely dependent on capillary forces.

8. The device of claim 1 wherein each of the microchannels has at least one internal surface that is at least partially coated with at least one insoluble material to enhance the capillary forces and minimize coagulation.

9. The device of claim 1 wherein the plurality of microchannels are fabricated in an array.

10. The device of claim 1 wherein the microchannels are fabricated in an array having approximately 50-150 microchannels formed in a maximum diameter of approximately 5 cm.

11. The device of claim 1 wherein each of the first plurality of microneedles is dimensioned for volumes of fluid in the range of about 50-500 nanoliters.

12. The device of claim 1 comprising a detector operable to determine when the fluid sample completely fills at least one microchannel such that the accumulation of the fluid sample with the associated microneedle may be terminated.

13. The device of claim 1 wherein at least one microchannel is in fluid communication with at least one reagent operable to assay for analytes selected from the group of (a) glucose, (b) cholesterol, (c) ethanol, (d) digoxin, (e) HDL cholesterol, (f) lithium, (g) sodium, (h) phenytoin, (i) therophylline, (j) cyclosporine, (k) cancer chemotheraphy drugs, (l) DNA, (m) RNA, (n) extended phenytonin sodium, (o) warfarin sodium, and (p) proteins derived from blood.

14. The device of claim 1 wherein at least two microchannels are associated with a single microneedle so that multiple assays can be performed using a single microneedle.

15. The device of claim 1 wherein at least one monitoring microchannel is sealed with a polymer.

16. The device of claim 1 wherein the plurality of microneedles, plurality of microchannels and the reagent are contained in a disposable cartridge.

17. The device of claim 16, further comprising a reusable module receiving the disposable cartridge therein.

18. The device of claim 17, wherein the disposable cartridge further comprises an electromechanical interface for the reusable module.

19. The device of claim 1, wherein each of the plurality of microneedles comprises an internal bore in direct fluid communication with a respective microchannel.

20. The device of claim 19, wherein each of the plurality of microchannels is disposed directly above a respective microneedle.

21. The device of claim 20, further comprising a cover at least partially enclosing at least one of the plurality of microchannels.

22. The device of claim 1, further comprising an optical sensor constructed and arranged to make colorimetric measurements for determining a concentration of the analyte contained in the fluid sample.

23. The device of claim 22, wherein each microchannel and the associated reagent define a reaction site, and the device further comprising a blood detection sensor constructed and arranged to detect the presence of blood at the reaction site.

24. The device of claim 23, wherein the blood detection sensor comprises the optical sensor, and the optical sensor is constructed and arranged to detect the presence of blood at the reaction site prior to the determination of the concentration of the analyte contained in the fluid sample.

* * * * *